(12) United States Patent
Takenoshita et al.

(10) Patent No.: US 8,718,749 B2
(45) Date of Patent: May 6, 2014

(54) VESSEL PULSE WAVE MEASUREMENT SYSTEM CONDUCTING VESSEL PULSE WAVE MEASUREMENT BY OBTAINING PULSATION WAVEFORM OF BLOOD VESSEL

(71) Applicant: Act Medical Service Co., Ltd., Fukushima (JP)

(72) Inventors: Seiichi Takenoshita, Fukushima (JP); Shintaro Chiba, Tokyo (JP); Yutaka Hata, Hyogo (JP); Tokuko Saito Wiedemann, El Cerrito, CA (US); Hiromichi Annoh, Fukushima (JP); Asako Yagi, Kanagawa (JP); Shinichi Takahashi, Fukushima (JP); Fukuto Handa, Fukushima (JP); Toshikuni Yajima, Fukushima (JP)

(73) Assignee: Act Medical Service Co., Ltd., Fukushima (JP)

( * ) Notice: Subject to any disclaimer, the term of this patent is extended or adjusted under 35 U.S.C. 154(b) by 0 days.

(21) Appl. No.: 13/853,487

(22) Filed: Mar. 29, 2013

(65) Prior Publication Data

US 2013/0296717 A1 Nov. 7, 2013

Related U.S. Application Data

(63) Continuation of application No. 13/562,655, filed on Jul. 31, 2012, now Pat. No. 8,483,805, which is a continuation of application No. PCT/JP2011/080339, filed on Dec. 27, 2011.

(30) Foreign Application Priority Data

Jan. 24, 2011 (JP) .................................. 2011-012106

(51) Int. Cl.
*A61B 6/00* (2006.01)

(52) U.S. Cl.
USPC ........... 600/473; 600/407; 600/474; 600/475; 600/476

(58) Field of Classification Search
USPC .......................................... 600/407, 473–480
See application file for complete search history.

(56) References Cited

U.S. PATENT DOCUMENTS

| 5,485,838 A | 1/1996 | Ukawa et al. |
| 5,676,140 A | 10/1997 | Ukawa et al. |

(Continued)

FOREIGN PATENT DOCUMENTS

| JP | 6-169892 | 6/1994 |
| JP | 9-145691 | 6/1997 |

(Continued)

OTHER PUBLICATIONS

International Search Report issued Apr. 17, 2012 in International (PCT) Application No. PCT/JP2011/080339.

(Continued)

*Primary Examiner* — James Kish
(74) *Attorney, Agent, or Firm* — Wenderoth, Lind & Ponack, L.L.P.

(57) ABSTRACT

A vessel pulse wave measurement system performs vessel pulse wave measurement using an optical probe circuit provided with an optical probe including a light emitting element and a light receiving element, a drive circuit, and a detection circuit. A measurement device directly and synchronously feeds back an electrical signal from the optical probe to the drive circuit as a drive signal to generate a self-oscillation signal from the detection circuit, and measures the self-oscillation signal as a vessel pulse wave signal. A controller controls an operating point of at least one of the detection circuit and the drive circuit such that the self-oscillation signal substantially reaches a maximum level thereof.

3 Claims, 21 Drawing Sheets

(56) References Cited

U.S. PATENT DOCUMENTS

| | | |
|---|---|---|
| 5,766,137 A | 6/1998 | Omata |
| 6,561,984 B1 | 5/2003 | Turcott |
| 6,731,967 B1 * | 5/2004 | Turcott .................. 600/407 |
| 7,324,848 B1 * | 1/2008 | Turcott .................. 607/17 |
| 2004/0162499 A1 | 8/2004 | Nagai et al. |
| 2010/0152560 A1 | 6/2010 | Turcott |

FOREIGN PATENT DOCUMENTS

| | | |
|---|---|---|
| JP | 2001-187032 | 7/2001 |
| JP | 2004-121668 | 4/2004 |
| JP | 2005-21477 | 1/2005 |
| JP | 2008-142254 | 6/2008 |
| WO | 2010/089893 | 8/2010 |

OTHER PUBLICATIONS

Motoaki Sugawara et al., "Hemorheology and Blood Flow", Corona Publishing Co., Ltd., pp. 120-121, Apr. 25, 2003, together with Partial translation.

English translation of International Preliminary Report on Patentability and Written Opinion mailed Aug. 8, 2013 in International (PCT) Application No. PCT/JP2011/080339.

* cited by examiner

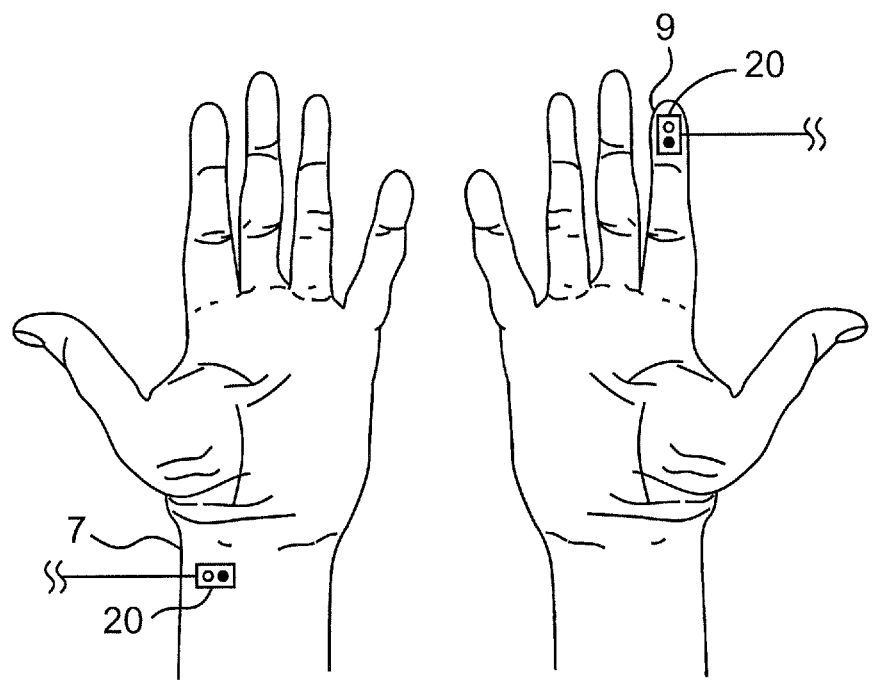
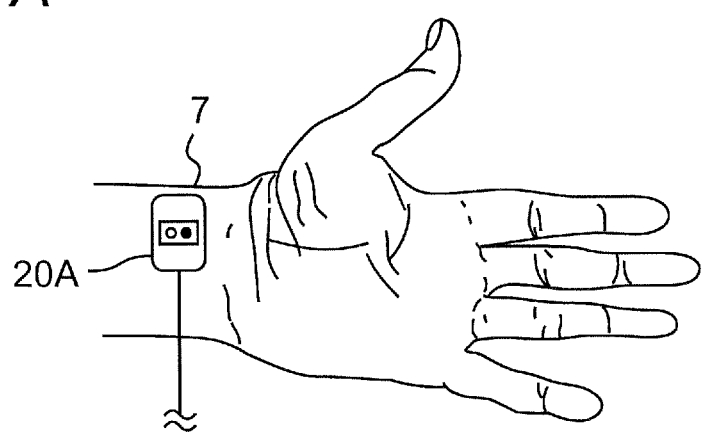

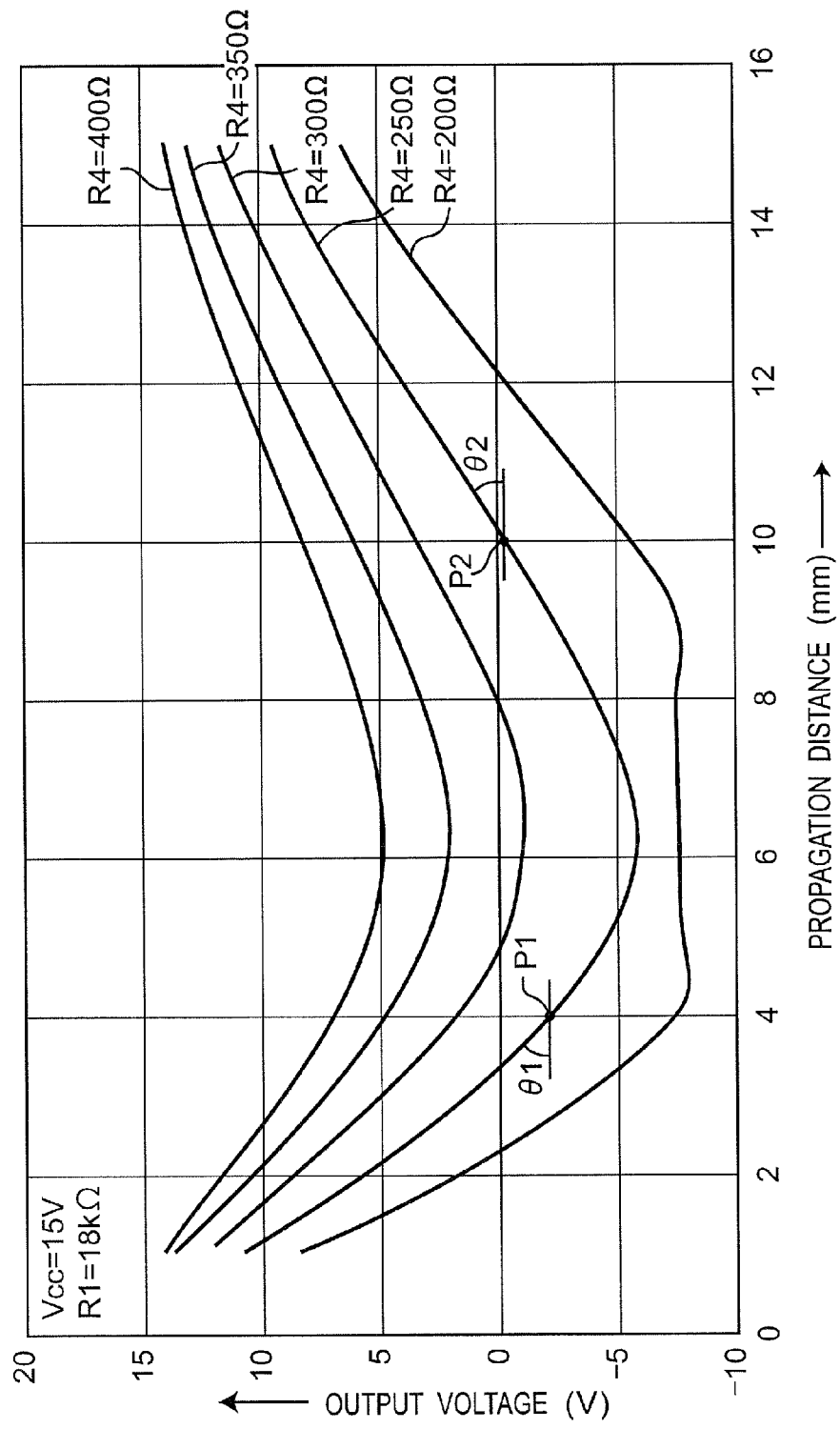

$$b_i = \frac{a_{i-4} + a_{i-3} + a_{i-2} + a_{i-1} + a_i}{5}$$

R-EOG A1
Chin-Ref
ELECTROCARDIOGRAM
ELECTROMYOGRAM
SNORING
RESPIRATORY WAVEFORM
SpO2
PRESENT SYSTEM

AWAKE DATA

R-EOG A1
Chin-Ref
ELECTROCARDIOGRAM
ELECTROMYOGRAM
SNORING
RESPIRATORY TEMPERATURE SENSOR
RESPIRATORY PRESSURE
CHEST FLUCTUATIONS
ABDOMEN FLUCTUATIONS
SpO2
PRESENT SYSTEM

APNEA DATA

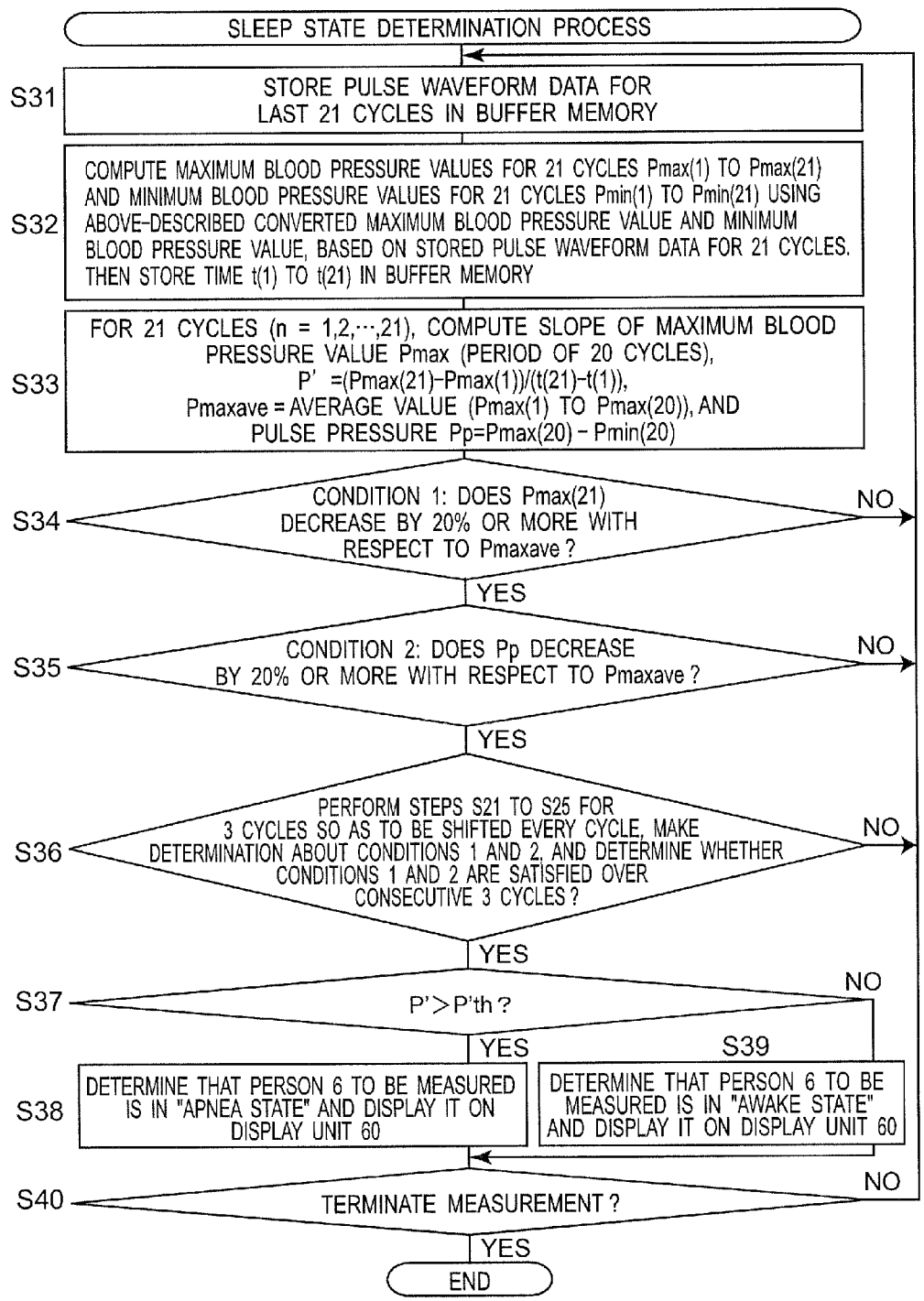

VESSEL PULSE WAVE MEASUREMENT SYSTEM CONDUCTING VESSEL PULSE WAVE MEASUREMENT BY OBTAINING PULSATION WAVEFORM OF BLOOD VESSEL

This is a continuation application based on PCT application No. PCT/JP2011/080339 as filed on Dec. 27, 2011, which claims priority to Japanese patent application No. JP 2011-012106 as filed Jan. 24, 2011, the contents of which are incorporated herein by reference.

BACKGROUND OF THE INVENTION

1. Field of the Invention

The present invention relates to a vessel pulse wave measurement system, and more particularly, to a vessel pulse wave measurement system that performs vessel pulse wave measurement by obtaining a pulsation waveform (hereinafter, referred to as a pulse wave) of a blood vessel using a light emitting element and a light receiving element.

2. Description of the Related Art

For techniques for evaluating properties of a material, a method using an oscillation has been known. Patent Document 1 discloses a method of converting phase change to frequency change, taking into account that in the difference in the properties of the material, a change in the phase of oscillation is greater than a change in the frequency of oscillation but the accuracy of phase measurement techniques is not always high. An apparatus using this method is configured to include an oscillator, an oscillation detection sensor, an amplifier, a phase shift circuit, and amount-of-frequency-change detection means. The oscillator oscillates and radiates ultrasound into the material, and the oscillation detection sensor detects a reflected wave from the material. The amplifier has an input terminal connected to a signal output terminal of the oscillation detection sensor, and the phase shift circuit is provided between an output terminal of the amplifier and an input terminal of the oscillator, and changes the frequency to shift the phase difference to zero when a phase difference occurs between an input waveform to the oscillator and an output waveform from the oscillation detection sensor. The amount-of-frequency-change detection means detects the amount of frequency change for shifting the phase difference to zero.

In the apparatus of Patent Document 1, specifically, a hardness measuring apparatus using a frequency deviation detection circuit is configured to include a contact element, an oscillator, a self-oscillation circuit, and a gain change correction circuit in order to accurately measure hardness information in a wide range from a soft object to be measured to a hard object to be measured. The self-oscillation circuit feeds back oscillation information of the oscillator to bring about a resonance state. The gain change correction circuit is provided in the self-oscillation circuit. The gain change correction circuit has a center frequency different from that of the self-oscillation circuit, and increases the gain in response to a change in the frequency.

In the above-described apparatus, the amount-of-frequency-change detection means shifts a phase difference caused by a difference in hardness to zero, and converts the resulting shifted phase difference to an amount of frequency change. The conversion uses a reference transfer function representing the relationship between the amplitude gain and phase of a reflected wave with respect to frequency, where the reference transfer function is obtained in advance. In addition, although ultrasonic oscillation is used as oscillation, instead of this, oscillation of an electrical signal in an electric circuit can be used. For example, a light emitting element is driven by a drive signal to radiate light, and a light receiving element detects the light and feeds back a detected signal as a drive signal of the light emitting element. Then a feedback loop is formed, and oscillation of an electrical signal flowing through the feedback loop can be used.

Namely, there is a signal delay between a drive signal of the light emitting element and an optical signal to be radiated, which is caused by the structure of the light emitting element, and likewise, there is also a signal delay between an optical signal entering the light receiving element and a detected signal outputted from the light receiving element, which is caused by the structure of the light receiving element. Therefore, if a feedback loop is formed by combining the light emitting element and the light receiving element, then self-oscillation occurs so as to make a phase difference, which is a delay therebetween zero. By providing the phase shift circuit disclosed in Patent Document 1 in the feedback loop, the phase difference can be converted to a frequency difference.

Then, the light from the light emitting element is allowed to radiate an object to be evaluated, and the light receiving element receives light reflected from the object. In this case, a feedback loop is formed, then the frequency of the self-oscillation circuit depends on a delay caused by the configuration of the light receiving element and the light emitting element and a delay caused by the properties of the material to be evaluated. Therefore, by providing a phase-shift circuit in the feedback loop and converting a phase difference by each frequency and observing the frequency difference, the properties of the material can be measured in a non-contact manner or non-invasive manner.

For example, Patent Document 2 describes a blood pressure measuring apparatus that includes a sensor unit, and a self-oscillation circuit. The sensor unit transmits infrared light into the body and receives a reflected wave in the body, and the self-oscillation circuit performs self-oscillation by feeding back an electrical signal based on the received reflected wave to a wave transmitting unit. The self-oscillation circuit includes a gain change correction circuit that changes gain in response to frequency change, and adjusts a phase difference between an input phase and an output phase to zero to promote feedback oscillation. A blood pressure can be calculated based on an oscillation frequency of the self-oscillation circuit obtained in the above-described manner.

In the apparatus of Patent Document 2, in order to perform measurement of blood pressure with high accuracy and to reduce burdens on a person to be measured, a wave transmitting unit converts an electrical signal and transmits an electromagnetic wave or ultrasonic wave such as infrared light into the body. Then a wave receiving unit receives a reflected wave in the body, and converts the reflected wave to an electrical signal. The frequency of the self-oscillation circuit measured by a frequency measuring unit is converted to a blood pressure value based on a correlation parameter invoked by a blood pressure computing unit, and a display unit sequentially provides display of the blood pressure value or a blood pressure waveform.

As mentioned above, according to the technique of the phase shift method, a pulsation waveform of a blood vessel can be accurately obtained using the light emitting element and the light receiving element. However, a living body, which is a target for measuring pulsation of a blood vessel, such as a person to be measured, does not always maintain a stable state during measurement. The living body may change his/her posture such as moving his/her arm having the light emitting element and the light receiving element attached thereto. In addition, if the attachment state of the light emitting element and the light receiving element is incomplete, then the attachment state may change during measurement.

Accordingly, a pulsation waveform may change gradually during measurement and may, for example, go out of a measurement range and a computing range. If the pulsation waveform thus shifts from the measurement range, then accurate vessel pulse wave measurement cannot be performed. In order to provide a vessel pulse wave measurement system capable of performing more accurate measurement to solve this problem, the inventors of this application proposed the following vessel pulse wave measurement system in Patent Document 3.

The vessel pulse wave measurement system of Patent Document 3 is characterized in that the system includes an optical probe, a pulsation waveform output unit, and an arithmetic processing unit. The optical probe is attached to a part suitable for obtaining pulsation of a blood vessel of a person to be measured. The pulsation waveform output unit is connected to the optical probe through an optical probe circuit, and outputs a pulsation waveform as a temporal change in frequency, using a phase shift method. A floating median setting processing module of the arithmetic processing unit has a function of amplifying the maximum amplitude value of periodic frequency data such that the maximum amplitude value has a predetermined ratio with respect to a computing range, and setting a median thereof as a median of the computing range in a floating manner, regardless of an absolute value thereof.

Further, Patent Document 4 proposes an abnormal respiration detection apparatus including abnormal respiration determination means for obtaining the number of pulses and pulse amplitude based on a pulse wave signal indicating the state of a pulse wave, and making a determination of abnormal respiration based on the number of pulses and the pulse amplitude. The apparatus is characterized by, for example, detecting abnormal respiration based on the ratio between pulse wave amplitude and the number of pulses per unit time, or detecting abnormal respiration based on a change in the number of respirations, a change in the number of pulses, and a change in oxygen saturation concentration in blood.

Prior art documents which related to the present invention are as follows.

Patent Document 1: Japanese patent laid-open publication No. JP 9-145691 A;
Patent Document 2: Japanese patent laid-open publication No. JP 2001-187032 A;
Patent Document 3: International publication No. WO 2010/089893;
Patent Document 4: Japanese patent laid-open publication No. JP 2004-121668 A;
Patent Document 5: Japanese patent laid-open publication No. JP 6-169892 A;
Patent Document 6: Japanese patent laid-open publication No. JP 2005-021477 A; and
Non-Patent Document 1: Motoaki Sugawara et al., "Hemorheology and Blood Flow", Corona Publishing Co., Ltd., pages 120-121, Apr. 25, 2003, together with Partial translation.

However, the apparatuses according to the prior art disclosed in the above-described Patent Documents 1 to 3 have such a problem that the apparatuses do not work almost at all on the measurement scene because of frequent occurrence of the case in which the apparatuses cannot obtain pulsation waveform data due to that the operation of obtaining pulsation of a blood vessel often becomes an unstable state, (a) in addition to a change in the attachment state of the light emitting element and the light receiving element, (b) according to the attachment part; for example, whether to attach the light emitting element and the light receiving element to the radial artery portion at the wrist or to a fingertip, (c) in addition, for example, according to the thickness of the skin of a thin person to be measured or a fat person to be measured, even if the light emitting element and the light receiving element are attached to the same part of the radial artery portion, and (d) further, according to the type of optical probe; for example, whether to use a reflective type optical probe using reflected light from a blood vessel or use a transmission type optical probe using transmitted light transmitted through a blood vessel.

In addition, the abnormal respiration detection apparatus according to the prior art disclosed in the Patent Document 4 has such a problem that the accuracy of detection of abnormal respiration is still low, in addition to the above-described problem.

SUMMARY OF THE INVENTION

A first object of the present invention is to solve the above-described problems and to provide a vessel pulse wave measurement system capable of obtaining pulsation waveform data and performing vessel pulse wave measurement, with a simpler configuration than that of the prior art, even in the case of different propagation distances of light from a light emitting element to a light receiving element.

In addition, a second object of the present invention is to solve the above-described problems and to provide a vessel pulse wave measurement system capable of detecting abnormal respiration using the above-described vessel pulse wave measurement system, with a simpler configuration and higher accuracy than those of the prior art.

Further, a third object of the present invention is to provide a vessel pulse wave measurement system capable of performing calibration to convert a blood pressure value voltage of a vessel pulse wave signal to a blood pressure value, using the above-described vessel pulse wave measurement system, with a simpler configuration and higher accuracy than those of the prior art.

In order to achieve the aforementioned objective, according to one aspect of the present invention, a vessel pulse wave measurement system is provided that performs vessel pulse wave measurement using an optical probe circuit. The optical probe circuit includes an optical probe, a drive circuit, and a detection circuit. The optical probe is configured to include a light emitting element that radiates light to a blood vessel through a skin, and a light receiving element that receives, through the skin, reflected light from the blood vessel or transmitted light through the blood vessel. The drive circuit drives the light emitting element based on an inputted drive signal, and the detection circuit converts the light received by the light receiving element into an electrical signal and outputs the electrical signal. The vessel pulse wave measurement system includes a measurement device, and a controller. The measurement device is configured to directly and synchronously feed back the electrical signal to the drive circuit as the drive signal, generate a self-oscillation signal from the detection circuit, and measure the self-oscillation signal as a vessel pulse wave signal. The controller is configured to control an operating point of at least one of the detection circuit and the drive circuit such that the self-oscillation signal substantially reaches a maximum level thereof.

In the above-mentioned vessel pulse wave measurement system, operating points of the drive circuit and the detection circuit in the optical probe circuit are determined by element values of the drive circuit and the detection circuit, respectively, and by the determination, an operating point in an electric characteristic representing a level of the electrical signal with respect to a propagation distance of light is determined, the propagation distance of light indicating a distance of light radiated from the light emitting element to reach the light receiving element. The controller controls the operating point in the electric characteristic by setting predetermined operating point initial values for the respective operating points of the detection circuit and the drive circuit, and then controlling the operating point of at least one of the detection circuit and the drive circuit such that the self-oscillation signal substantially reaches a maximum level thereof.

In addition, in the above-mentioned vessel pulse wave measurement system, the electric characteristic has a predetermined extreme value for the level of the electrical signal at a predetermined boundary propagation distance. The controller controls the detection circuit and the drive circuit to operate in at least one range of a first propagation distance range and a second propagation distance range, where the first propagation distance range is shorter than the boundary propagation distance, and the second propagation distance range is longer than the boundary propagation distance.

Further, in the above-mentioned vessel pulse wave measurement system, the controller includes a storage device, and a first switch. The storage device is configured to store in advance operating point initial values of the detection circuit and the drive circuit corresponding to predetermined operating point initial values in the first propagation distance range, and store in advance operating point initial values of the detection circuit and the drive circuit corresponding to predetermined operating point initial values in the second propagation distance range. The first switch is configured to select one of the operating point initial values in the first propagation distance range and the operating point initial values in the second propagation distance range. The controller sets the operating points of the detection circuit and the drive circuit, using the operating point initial values of the detection circuit and the drive circuit corresponding to the operating point initial values selected by the first switch.

Furthermore, in the above-mentioned vessel pulse wave measurement system, the optical probe circuit includes a plurality of pairs of a light emitting element and a light receiving element, where the pairs have different boundary propagation distances. The storage device stores in advance, for each of the pairs, operating point initial values of the detection circuit and the drive circuit corresponding to predetermined operating point initial values in the electric characteristic. The controller includes a second switch for selecting one of the plurality of pairs, and the controller sets operating points of the detection circuit and the drive circuit, using the operating point initial values of the detection circuit and the drive circuit of the pair selected by the second switch.

Still further, in the above-mentioned vessel pulse wave measurement system, the measurement device computes a plurality of determination parameters based on the measured vessel pulse wave signal for a predetermined number of cycles, and determines whether a person to be measured is in one of an awake state and an apnea state, based on the plurality of determination parameters, the plurality of determination parameters including a gradient of a maximum blood pressure value with respect to time, an average value of the maximum blood pressure values, and a pulse pressure, which is a difference between a maximum blood pressure value and a minimum blood pressure value.

Still more further, in the above-mentioned vessel pulse wave measurement system, the measurement device determines that the person to be measured is in an awake state, (a) when a maximum blood pressure value at a predetermined time decreases by a predetermined first threshold proportion or more with respect to the average value of the maximum blood pressure value, (b) when the pulse pressure decreases by a predetermined second threshold proportion or more with respect to the average value of the maximum blood pressure value during a predetermined number of consecutive cycles, and (c) when the gradient of the maximum blood pressure value with respect to the time exceeds a predetermined threshold value. The measurement device determines that the person to be measured is in an apnea state when the gradient is equal to or smaller than the threshold value.

Still furthermore, in the above-mentioned vessel pulse wave measurement system, the measurement device further includes a pressure sheet sensor provided between the optical probe circuit and a pressing portion provided on the optical probe circuit, and the measurement device further includes a calibration part. When the vessel pulse wave signal is measured and a stress is applied to the optical probe circuit on the blood vessel by pressure applied to the pressing portion by a pressure actuator or by pressure applied to the pressing portion by a human and then the vessel pulse wave signal is not measured any more, the calibration part stores a voltage value of the vessel pulse wave signal obtained immediately before the vessel pulse wave signal is not measured, as a maximum blood pressure value voltage. The calibration part stores a detected pressure value of the pressure sheet sensor as a maximum blood pressure value, and then, when the vessel pulse wave signal is measured by reducing the pressure, the calibration part stores a voltage value of the vessel pulse wave signal obtained immediately after the vessel pulse wave signal is measured, as a minimum blood pressure value voltage. The calibration part stores a detected pressure value of the pressure sheet sensor as a minimum blood pressure value. The calibration part creates a conversion equation representing conversion from a blood pressure value voltage to a blood pressure value, based on the stored maximum blood pressure value voltage and maximum blood pressure value corresponding to the stored maximum blood pressure value voltage, and the stored minimum blood pressure value voltage and minimum blood pressure value corresponding to the stored minimum blood pressure value voltage, thereby performing calibration to convert a blood pressure value voltage of the vessel pulse wave signal to a blood pressure value, using the conversion equation.

According to another aspect of the present invention, there is provided a vessel pulse wave measurement system including a measurement device for measuring a vessel pulse wave signal by performing vessel pulse wave measurement, using an optical probe circuit. The optical probe circuit includes an optical probe, a drive circuit, and a detection circuit. The optical probe is configured to include a light emitting element that radiates light to a blood vessel through a skin, and a light receiving element that receives, through the skin, reflected light from the blood vessel or transmitted light through the blood vessel. The drive circuit drives the light emitting element based on a drive signal to be inputted, and the detection circuit that converts the light received by the light receiving element to an electrical signal and outputs the electrical signal. The measurement device further includes a pressure sheet sensor provided between the optical probe circuit and a pressing portion provided on the optical probe circuit, and the measurement device further includes a calibration part. When the vessel pulse wave signal is measured and a stress is applied to the optical probe circuit on the blood vessel by pressure applied to the pressing portion by a pressure actuator or by pressure applied to the pressing portion by a human and then the vessel pulse wave signal is not measured any more, the calibration part stores a voltage value of the vessel pulse wave signal obtained immediately before the vessel pulse wave signal is not measured, as a maximum blood pressure value voltage. The calibration part stores a detected pressure value of the pressure sheet sensor as a maximum blood pressure value, and then, when the vessel pulse wave signal is measured by reducing the pressure, the calibration part stores a voltage value of the vessel pulse wave signal obtained immediately after the vessel pulse wave signal is measured, as a minimum blood pressure value voltage. The calibration part stores a detected pressure value of the pressure sheet sensor as a minimum blood pressure value. The calibration part creates a conversion equation representing conversion from a blood pressure value voltage to a blood pressure value, based on the stored maximum blood pressure value voltage and maximum blood pressure value corresponding to the stored maximum blood pressure value voltage, and the stored minimum blood pressure value voltage and minimum blood pressure value corresponding to the stored minimum blood pressure value voltage, thereby performing calibration to convert a blood pressure value voltage of the vessel pulse wave signal to a blood pressure value, using the conversion equation.

According to the vessel pulse wave measurement system, the measurement device is configured to directly and synchronously feed back the electrical signal to the drive circuit as the drive signal, generate a self-oscillation signal from the detection circuit, and measure the self-oscillation signal as a vessel pulse wave signal. The controller is configured to control an operating point of at least one of the detection circuit and the drive circuit such that the self-oscillation signal substantially reaches a maximum level thereof. In this case, preferably, operating points of the drive circuit and the detection circuit in the optical probe circuit are determined by element values of the drive circuit and the detection circuit, respectively, and by the determination, an operating point in an electric characteristic representing a level of the electrical signal with respect to a propagation distance of light is determined, the propagation distance of light indicating a distance of light radiated from the light emitting element to reach the light receiving element. The controller controls the operating point in the electric characteristic by setting predetermined operating point initial values for the respective operating points of the detection circuit and the drive circuit, and then controlling the operating point of at least one of the detection circuit and the drive circuit such that the self-oscillation signal substantially reaches a maximum level thereof. Therefore, even in the case of different propagation distances of light from the light emitting element to the light receiving element, pulsation waveform data can be obtained and vessel pulse wave measurement can be performed with a simpler configuration than that of the prior art.

In addition, in the above-mentioned vessel pulse wave measurement system, the electric characteristic has a predetermined extreme value for the level of the electrical signal at a predetermined boundary propagation distance. The controller controls the detection circuit and the drive circuit to operate in at least one range of a first propagation distance range and a second propagation distance range, where the first propagation distance range is shorter than the boundary propagation distance, and the second propagation distance range is longer than the boundary propagation distance. In this case, the controller includes a storage device, and a first switch. The storage device is configured to store in advance operating point initial values of the detection circuit and the drive circuit corresponding to predetermined operating point initial values in the first propagation distance range, and store in advance operating point initial values of the detection circuit and the drive circuit corresponding to predetermined operating point initial values in the second propagation distance range. The first switch is configured to select one of the operating point initial values in the first propagation distance range and the operating point initial values in the second propagation distance range. The controller sets the operating points of the detection circuit and the drive circuit, using the operating point initial values of the detection circuit and the drive circuit corresponding to the operating point initial values selected by the first switch. Therefore, by selectively switching over the operating point, focusing on the boundary propagation distance, even in the case of different propagation distances of light from the light emitting element to the light receiving element, pulsation waveform data can be obtained and vessel pulse wave measurement can be performed with a simpler configuration than that of the prior art.

Furthermore, in the above-mentioned vessel pulse wave measurement system, the optical probe circuit includes a plurality of pairs of a light emitting element and a light receiving element, where the pairs have different boundary propagation distances. The storage device stores in advance, for each of the pairs, operating point initial values of the detection circuit and the drive circuit corresponding to predetermined operating point initial values in the electric characteristic. The controller includes a second switch for selecting one of the plurality of pairs, and the controller sets operating points of the detection circuit and the drive circuit, using the operating point initial values of the detection circuit and the drive circuit of the pair selected by the second switch. Therefore, by selectively switching over the operating point, focusing on a boundary propagation distance at which pulsation waveform data cannot be obtained almost at all, even in the case of different propagation distances of light from the light emitting element to the light receiving element, pulsation waveform data can be obtained and vessel pulse wave measurement can be performed with a simpler configuration than that of the prior art.

Still further, in the above-mentioned vessel pulse wave measurement system, the measurement device computes a plurality of determination parameters based on the measured vessel pulse wave signal for a predetermined number of cycles, and determines whether a person to be measured is in one of an awake state and an apnea state, based on the plurality of determination parameters, the plurality of determination parameters including a gradient of a maximum blood pressure value with respect to time, an average value of the maximum blood pressure values, and a pulse pressure, which is a difference between a maximum blood pressure value and a minimum blood pressure value. In this case, preferably, the measurement device determines that the person to be measured is in an awake state, (a) when a maximum blood pressure value at a predetermined time decreases by a predetermined first threshold proportion or more with respect to the average value of the maximum blood pressure value, (b) when the pulse pressure decreases by a predetermined second threshold proportion or more with respect to the average value of the maximum blood pressure value during a predetermined number of consecutive cycles, and (c) when the gradient of the maximum blood pressure value with respect to the time exceeds a predetermined threshold value. The measurement device determines that the person to be measured is in an apnea state when the gradient is equal to or smaller than the threshold value. Therefore, by using the above-described vessel pulse wave measurement system, abnormal respiration such as an apnea state can be detected with a simpler configuration and higher accuracy than those of the prior art.

Still furthermore, in the above-mentioned vessel pulse wave measurement system, the measurement device further includes a pressure sheet sensor provided between the optical probe circuit and a pressing portion provided on the optical probe circuit, and the measurement device further includes a calibration part. When the vessel pulse wave signal is measured and a stress is applied to the optical probe circuit on the blood vessel by pressure applied to the pressing portion by a pressure actuator or by pressure applied to the pressing portion by a human and then the vessel pulse wave signal is not measured any more, the calibration part stores a voltage value of the vessel pulse wave signal obtained immediately before the vessel pulse wave signal is not measured, as a maximum blood pressure value voltage. The calibration part stores a detected pressure value of the pressure sheet sensor as a maximum blood pressure value, and then, when the vessel pulse wave signal is measured by reducing the pressure, the calibration part stores a voltage value of the vessel pulse wave signal obtained immediately after the vessel pulse wave signal is measured, as a minimum blood pressure value voltage. The calibration part stores a detected pressure value of the pressure sheet sensor as a minimum blood pressure value. The calibration part creates a conversion equation representing conversion from a blood pressure value voltage to a blood pressure value, based on the stored maximum blood pressure value voltage and maximum blood pressure value corresponding to the stored maximum blood pressure value voltage, and the stored minimum blood pressure value voltage and minimum blood pressure value corresponding to the stored minimum blood pressure value voltage, thereby performing calibration to convert a blood pressure value voltage of the vessel pulse wave signal to a blood pressure value, using the conversion equation. Therefore, the above-described vessel pulse wave measurement system can perform calibration to convert a blood pressure value voltage of a vessel pulse wave signal to a blood pressure value, by extremely simpler calibration and with higher accuracy than that of the prior art.

BRIEF DESCRIPTION OF THE DRAWINGS

These and other objects and features of the present invention will become apparent from the following description taken in conjunction with the preferred embodiments thereof with reference to the accompanying drawings throughout which like parts are designated by like reference numerals, and in which:

FIG. 6A is a front view showing an example of attachment of the light emitting and receiving sensor of the optical probe circuit 20 to a radial artery portion 7 at the wrist of a person to be measured;

FIG. 6B is a front view showing an example of attachment of the light emitting and receiving sensor of the optical probe circuit 20 to a fingertip 9 of the person to be measured;

FIG. 7A is a front view showing exemplary attachment of an optical probe circuit 20A including a pressure sheet sensor and a light emitting and receiving sensor, according to a first modified embodiment;

FIG. 10 is a graph showing output voltage with respect to the propagation distance of light for a power supply voltage Vcc=15 V and a resistor R1=18 kΩ and when a resistor R4 is changed in the optical probe circuit 20 of FIGS. 5A and 5B;

FIG. 21 is a flowchart showing a sleep state determination process, which is performed by a sleep state determination processing module 53 of the apparatus controller 50 of FIG. 1.

DETAILED DESCRIPTION OF THE PREFERRED EMBODIMENTS

Figure 1:
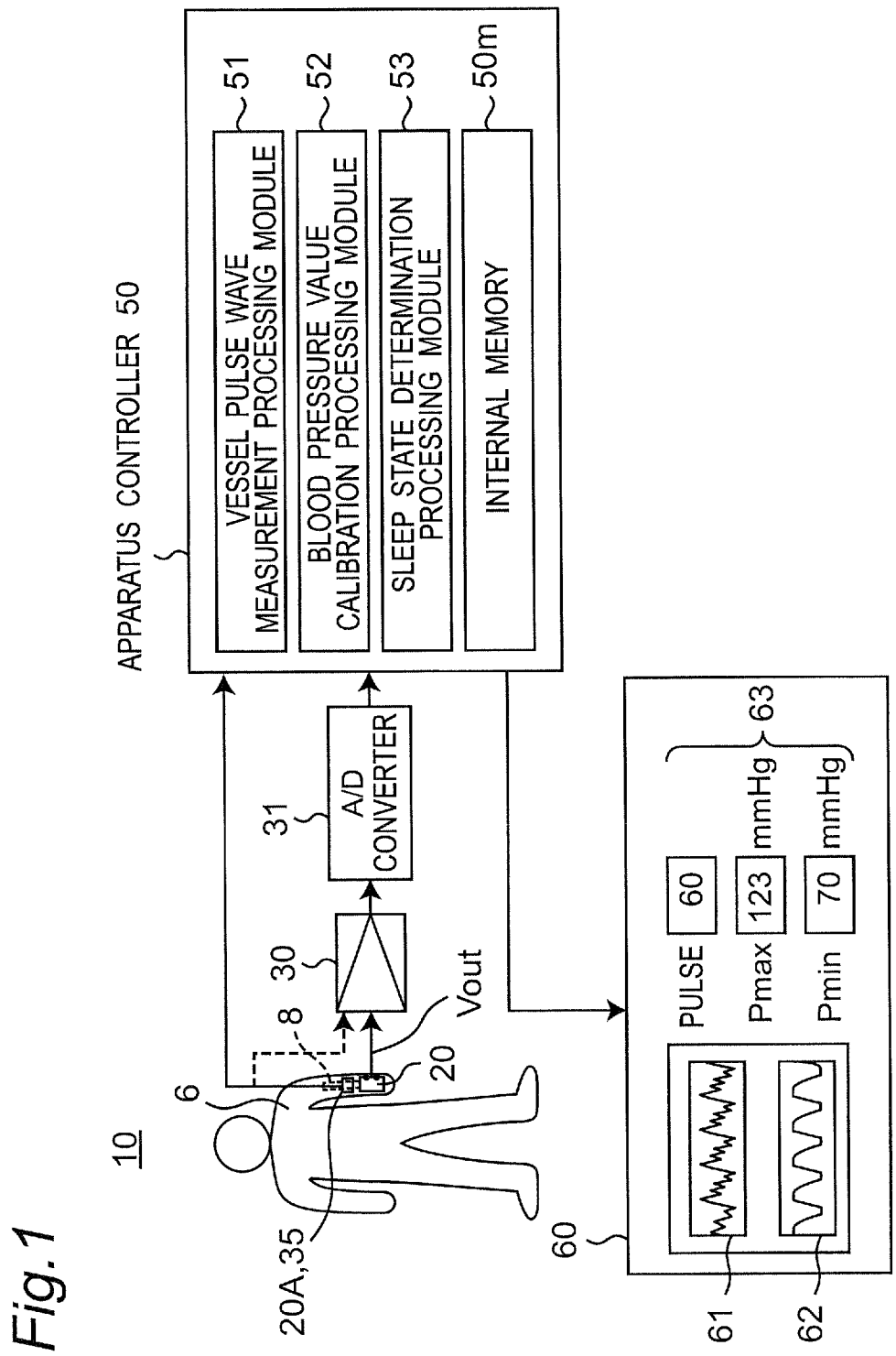
FIG. 1 is a block diagram showing a configuration of a vessel pulse wave measurement system according to an embodiment of the present invention.

Embodiments according to the present invention will be described below with reference to the drawings. It is noted that in each of the following embodiments, like components are denoted by the same reference characters. Although a pulse wave of a human blood vessel will be described in the following as a measurement target, the target can be any as long as the target is a pulse wave of a living body blood vessel and thus animals or the like other than humans can be used as the target. In addition, although in the following, as vessel pulse wave measurement, measurement of a pulse, a maximum blood pressure, and a minimum blood pressure will be described, any other measurement may be performed using a pulsation waveform of a blood vessel. For example, a volume corresponding to the volume of blood flow may be measured from an integral value of a pulse waveform and measurement for evaluating blood vessel flexibility from a differential value of a pulsation waveform may be performed. The materials, shapes, and dimensions described below are examples and thus they may be appropriately changed according to the purpose of use.

As a result of the inventors performing extensive research to solve the above-described "problem that the apparatuses according to the prior art disclosed in the above-described Patent Documents 1 to 3 do not work almost at all on the measurement scene because of frequent occurrence of the case in which the apparatuses cannot obtain pulsation waveform data due to the operation of obtaining pulsation of a blood vessel often becoming an unstable state, (a) in addition to a change in the attachment state of the light emitting element and the light receiving element, (b) according to the attachment part; for example, whether to attach the light emitting element and the light receiving element to the radial artery portion at the wrist or to a fingertip, (c) in addition, for example, according to the thickness of the skin of a thin person to be measured or a fat person to be measured, even if the light emitting element and the light receiving element are attached to the same part of the radial artery portion, and (d) further, according to the type of optical probe; for example, whether to use a reflective type optical probe using reflected light from a blood vessel or use a transmission type optical probe using transmitted light transmitted through a blood vessel", the inventors have focused on that these changes bring about a change in the propagation distance of light from the light emitting element to the light receiving element, and have conducted experiments in a manner described in detail later. Based on the results of the experiments, the inventors have ended up researching and developing the following vessel pulse wave measurement system capable of operating stably regardless of the above-described changes in conditions.

FIG. 1 is a block diagram showing a configuration of a vessel pulse wave measurement system according to an embodiment of the present invention. Referring to FIG. 1, a person 6 to be measured who is a target for measuring blood pressure, etc., and a blood vessel 8 in which blood pressure is actually measured, are shown in FIG. 1 though they not the components of a vessel pulse wave measurement system 10. It is noted that in the following drawings, depiction of the skin of the person 6 to be measured is omitted. The vessel pulse wave measurement system 10 according to the present embodiment is provided for performing pulse wave measurement by acquiring a pulsation waveform of the blood vessel 8 using an optical probe 12 having a light emitting element and a light receiving element, instead of a conventionally used cuff pressure method in which Korotkoff sounds are measured or invasive method in which the pressure in a blood vessel is directly measured by insertion and invasion of a catheter having a pressure sensor coupled thereto, into an artery.

The vessel pulse wave measurement system 10 is configured to include the following:

(a) an optical probe circuit 20 (or 20A or 20B) which includes the optical probe 12 to be attached to a part suitable for obtaining pulsation of the blood vessel 8 of the person 6 to be measured and which drives the light emitting element composing the optical probe 12 to allow the light emitting element to radiate light, and detects reflected light, which is reflected by the blood vessel 8, by the light receiving element through the skin;

(b) an amplifier 30 which amplifies an output voltage Vout from the optical probe circuit 20 (or 26);

(c) an A/D converter 31 which A/D-converts an output voltage from the amplifier 30 to digital data;

(d) an apparatus controller 50, which is a control apparatus such as a digital computer including an internal memory 50m, where the apparatus controller 50 includes a vessel pulse wave measurement processing module 51, a blood pressure value calibration processing module 52, and a sleep state determination processing module 53, and the apparatus controller 50 generates vessel pulse wave data by processing the digital data from the A/D converter 31 and performs a blood pressure value calibration process (FIG. 19), a vessel pulse wave measurement process (FIG. 20), and a sleep state determination process (FIG. 21) on the vessel pulse wave data; and (e) a display unit 60, which is, for example, a display or printer, where the display unit 60 provides, based on output data from the apparatus controller 50, pulsation waveform display (pulsation waveform display 61 obtained after a moving average process and pulsation waveform display 62 obtained after a low-pass filter process) and display 63 of measured values of a vessel pulse wave (a pulse, a maximum blood pressure value Pmax, and a minimum blood pressure value Pmin).

It is noted that an output voltage Vout from an optical probe circuit 20, 20A (FIGS. 7A and 9A) including a pressure sheet sensor 35 and a pressure actuator 36 is outputted to the amplifier 30, pressure value data from the pressure sheet sensor 35 is outputted to the apparatus controller 50, and a control signal to the pressure actuator 36 is outputted from the apparatus controller 50. In addition, in the case of only the pressure sheet sensor 35 (FIG. 7B), an optical probe circuit 20 is connected to the apparatus controller 50.

Figure 2:
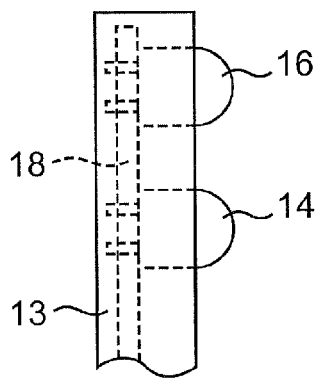
FIG. 2 is a side view showing a configuration of a reflective type optical probe 12 of an optical probe circuit 20 of FIG. 1.

FIG. 2 is a side view showing a configuration of the reflective type optical probe 12 the optical probe circuit 20 of FIG. 1. The optical probe 12 is configured such that a light emitting element 14 and a light receiving element 16 are mounted and disposed on a circuit board 18 in a predetermined holding unit 13. The holding unit 13 is a member including therein the circuit board 18 and having the light emitting element 14 and the light receiving element 16 disposed such that a light radiating portion of the light emitting element 14 and a light detecting portion of the light receiving element 16 project from a surface thereof, and is made of, for example, an appropriate plastic material formed into a shape. For the light emitting element 14, a Light Emitting Diode (LED) can be used and, for example, an infrared LED is used. In addition, for the light receiving element 16, a photodiode or phototransistor is used.

It is preferred that the light emitting element 14 and the light receiving element 16 be disposed close to each other, but in order to prevent light from the light emitting element 14 from directly entering the light receiving element 16, it is preferred to provide a structural device such as providing a light shielding wall therebetween. Alternatively, lenses may be provided to the light emitting element 14 and the light receiving element 16 to increase directivity. Although in the example of FIG. 2, one light emitting element 14 and one light receiving element 16 are provided, a plurality of light emitting elements 14 and a plurality of light receiving elements 16 may be provided. In addition, a plurality of light emitting elements 14 may be disposed to surround the light receiving element 16. The optical probe 12 is attached to a part suitable for detecting pulses of the blood vessel 8 of the person 6 to be measured, by an appropriate band, tape, or the like, which is not shown. Although FIG. 1 shows a state in which the optical probe 12 is attached to a radial artery portion 7 at the wrist, in addition to this, the optical probe 12 may be attached to parts such as a brachial artery portion corresponding to the inside of the elbow of the arm, a fingertip, and near the heart.

Figure 3:
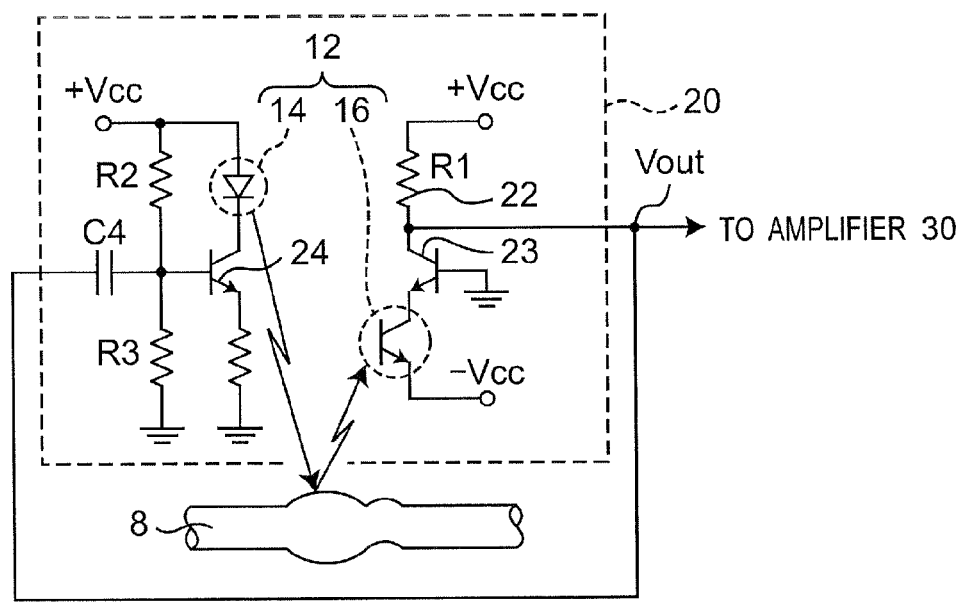
FIG. 3 is a circuit diagram showing a configuration of the optical probe circuit 20 of FIG. 1.

FIG. 3 is a circuit diagram showing a configuration of the optical probe circuit 20 of FIG. 1. The optical probe circuit 20 is configured by a drive circuit for the light emitting element 14 and a detection circuit for the light receiving element 16, and composes a self-oscillation circuit by synchronous feedback by directly inputting an output signal from the detection circuit to the drive circuit.

The drive circuit for the light emitting element 14 uses a configuration in which the light emitting element 14 and a drive transistor 24 are connected in series between a power supply voltage Vcc and a ground, and a base, which is a control terminal of the drive transistor 24 has a predetermined bias condition. In this configuration, when an input signal to the base of the drive transistor 24 goes high, the drive transistor 24 is turned on and thus a drive current flows through the light emitting element 14. With this, the light emitting element 14 emits light and the light is radiated toward the blood vessel 8 through the skin. In addition, the detection circuit for the light receiving element 16 uses a configuration in which a load resistor 22, a transistor 23, and the light receiving element 16 are connected in series between a positive power supply voltage Vcc and a negative power supply voltage −Vcc. In this configuration, by the light receiving element 14 receiving, through the skin, reflected light from the blood vessel 8 irradiated with the light from the light emitting element 14, a photocurrent is produced in the light receiving element 16. The magnitude of the photocurrent is outputted as a signal of an output voltage Vout (output voltage signal) corresponding to the magnitude of a current flowing through the load resistor 22. It is noted that the signal of an output voltage Vout is a self-oscillation signal and thus is an alternating current signal.

Referring to FIG. 1, an output voltage signal from the optical probe circuit 20 composing the self-oscillation circuit is outputted to the apparatus controller 50 through the amplifier 30 and the A/D converter 31. As mentioned above, when light from the light emitting element 14 is reflected by the blood vessel 8 (specifically, for example, a blood vessel wall of a blood vessel filled with blood containing oxygenated hemoglobin) and the light receiving element 16 receives the reflected light from the blood vessel 8, assuming that there is no influence of light directly entering the light receiving element 16 from the light emitting element 14, an output voltage signal from the optical probe circuit 20, namely, an output voltage Vout, changes according to the propagation distance of light (which means a distance of light radiated from the light emitting element 14 to reach the light receiving element 16). Thus, when the blood vessel 8 changes by pulsation, the output voltage Vout changes, namely, the output voltage Vout changes in response to the change in pulsation.

In the prior art such as Patent Documents 1 to 3, since a large change in output voltage is unable to be obtained, a change in the frequency thereof is converted to a voltage change to detect a change in pulsation. On the other hand, in the present embodiment, as shown in FIG. 3, an output signal from the detection circuit in the optical probe circuit 20 is directly and synchronously fed back as an input signal to the drive circuit, for self-oscillation to generate a self-oscillation signal, and as will be described in detail later, a sensor controller 25 performs setting by controlling an output voltage Vout (the amplitude (the amount of change) of the self-oscillation signal, which is an alternating current signal) such that the output voltage Vout substantially reaches the maximum thereof. Then a pulsation waveform can be extremely easily obtained.

Figure 4:
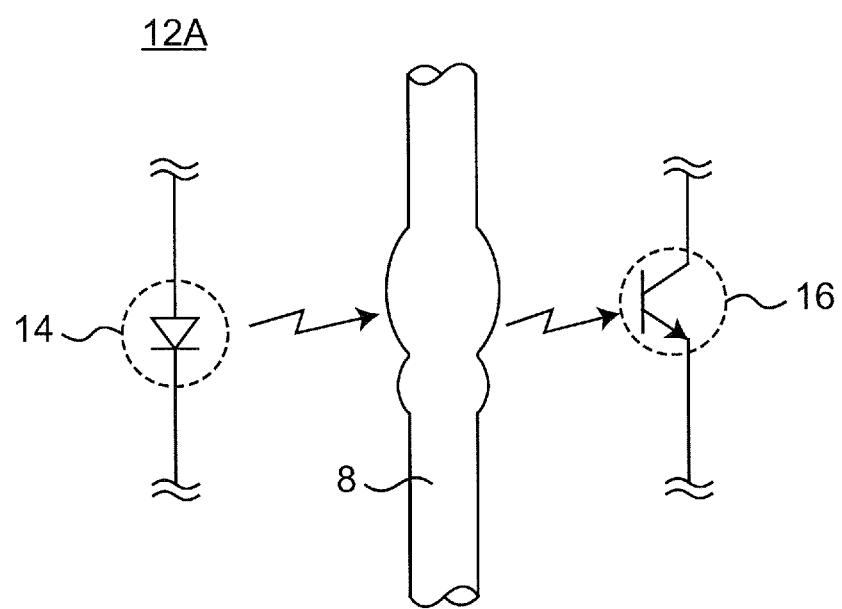
FIG. 4 is a schematic diagram showing a configuration of a transmission type optical probe 12A according to a modified embodiment.

FIG. 4 is a schematic diagram showing a configuration of a transmission type optical probe 12A according to a modified embodiment. The transmission type optical probe 12A of FIG. 4 may be used instead of the reflective type optical probe 12 of FIG. 3. Though the propagation distance of transmitted light is longer than the propagation distance of light in the reflective type optical probe 12 of FIG. 3, vessel pulse wave measurement can be performed using the transmission type optical probe 12A in the same manner.

Figure 5A:
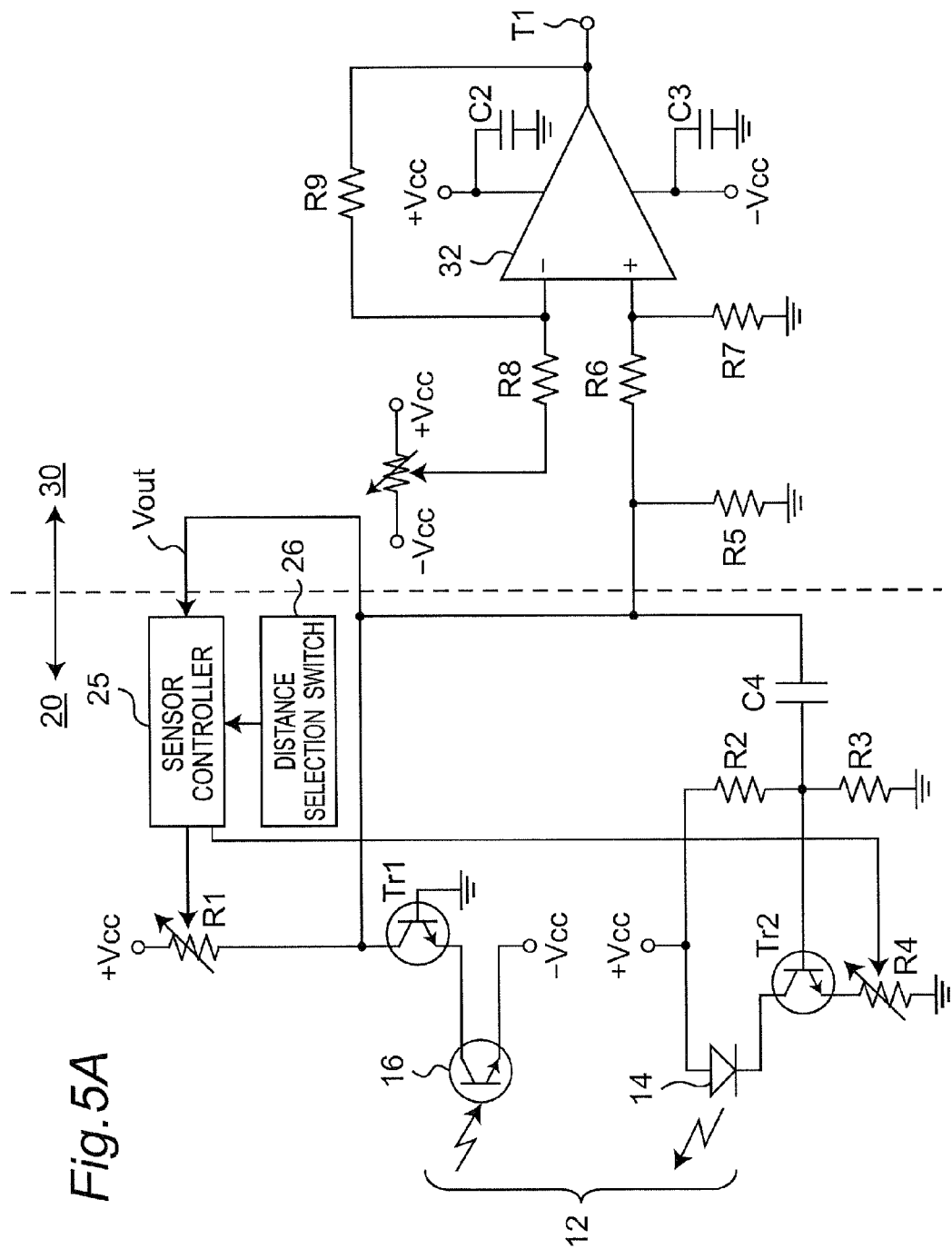
FIG. 5A is a circuit diagram showing a specific example of the optical probe circuit 20 and an amplifier 30 of FIG. 1.

FIG. 5A is a circuit diagram showing a specific example of the optical probe circuit 20 and the amplifier 30 of FIG. 1. Referring to FIG. 5A, the optical probe circuit 20 is configured to include a light emitting element 14 and a drive circuit therefor; a light receiving element 16 and a detection circuit therefor; and a sensor controller 25 that controls the operating points of the drive circuit and the detection circuit. In addition, T1 denote an output terminal.

The sensor controller 25 is a control apparatus such as a digital computer, and includes a distance selection switch 26. The distance selection switch 26 is a switch for setting initial values (specifically, the initial values of resistors R1 and R4) that determine the operating points of the drive circuit and the detection circuit, and is configured to be able to select, for example, "large distance" or "small distance". This is because, as will be described in detail later with reference to FIGS. 10 to 13, a large value can be obtained as a change in output voltage (the amplitude of a self-oscillation signal) with respect to a change in propagation distance, in regions around a predetermined boundary propagation distance serving as a boundary and having an extreme value of an output voltage in electric characteristics shown in FIGS. 10 to 13, and thus, a pulse wave voltage can be obtained. Therefore, a measurable propagation distance can be expanded. Namely, the "large distance" is used when vessel pulse wave measurement is performed at a propagation distance longer than the boundary propagation distance, and the "small distance" is used when vessel pulse wave measurement is performed at a propagation distance shorter than the boundary propagation distance.

Figure 18:
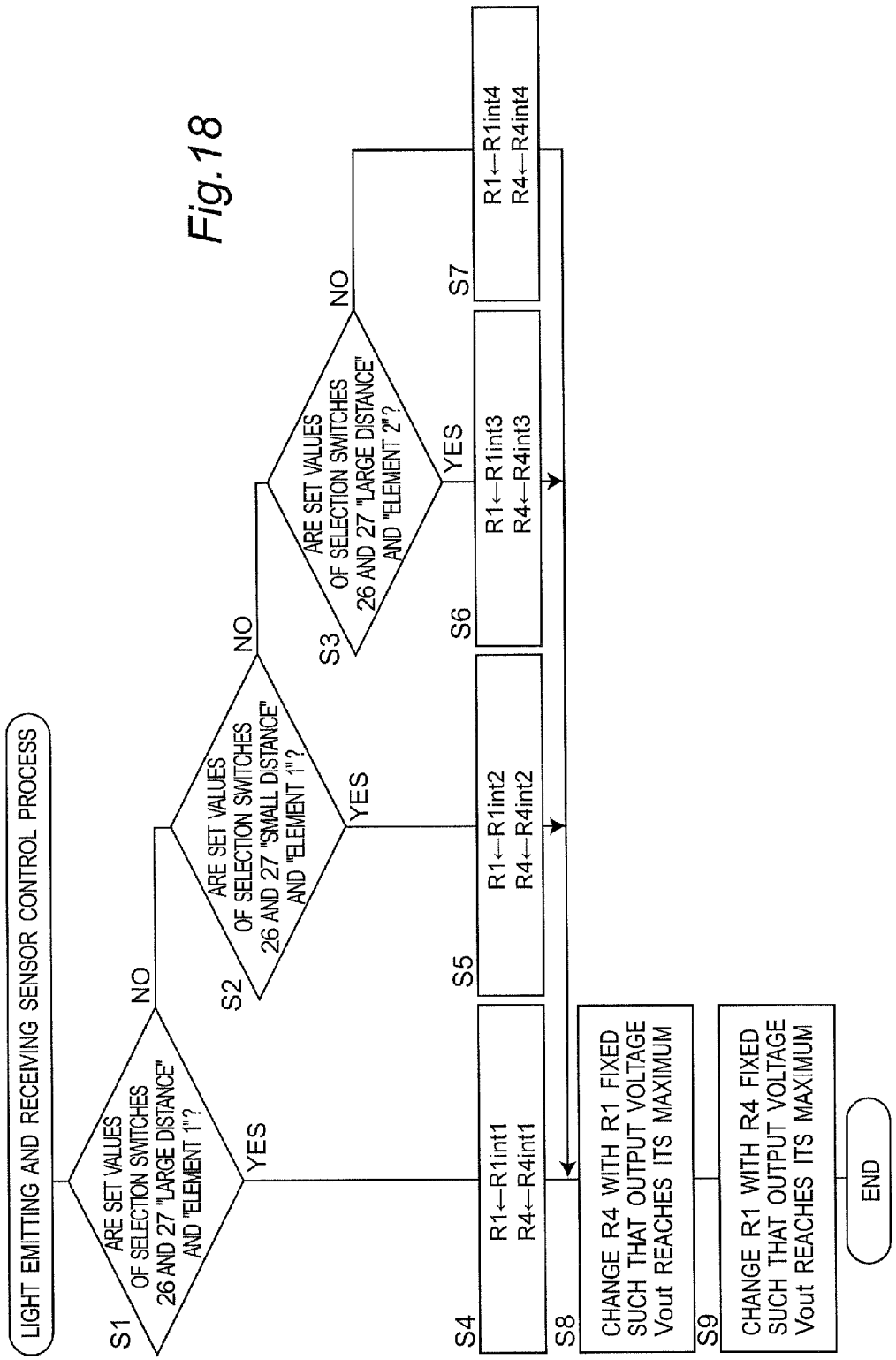
FIG. 18 is a flowchart showing a light emitting and receiving sensor control process, which is performed by a sensor controller 25 of FIGS. 5A and 5B.

According to a light emitting and receiving sensor control process of FIG. 18, the sensor controller 25 sets predetermined initial values for the resistors R1 and R4 and then performs control to change the resistance values of the resistors R1 and R4 such that an output voltage Vout from the optical probe circuit 20 substantially reaches the maximum thereof. In addition, a capacitor C4 in the optical probe circuit 20 is provided for blocking a direct current and is provided to determine a frequency characteristic of a self-oscillation signal in a self-oscillation circuit including synchronous feedback formed by the detection circuit and the drive circuit. The capacitor C4 is configured such that, for example, when the maximum heartbeat frequency is 240 heartbeats/minute, a low-pass filter with a cutoff frequency of 4 Hz is inserted. Further, the amplifier 30 is configured to include, for example, an operational amplifier 32 in a well-known manner.

Although the optical probe circuit 20 described above uses an output voltage Vout from the detection circuit for the light receiving element 16, as a drive signal to the drive circuit for the light emitting element 14, the present invention is not limited thereto and an electrical signal such as an output current may be used as a drive signal to the drive circuit for the light emitting element 14.

Figure 5B:
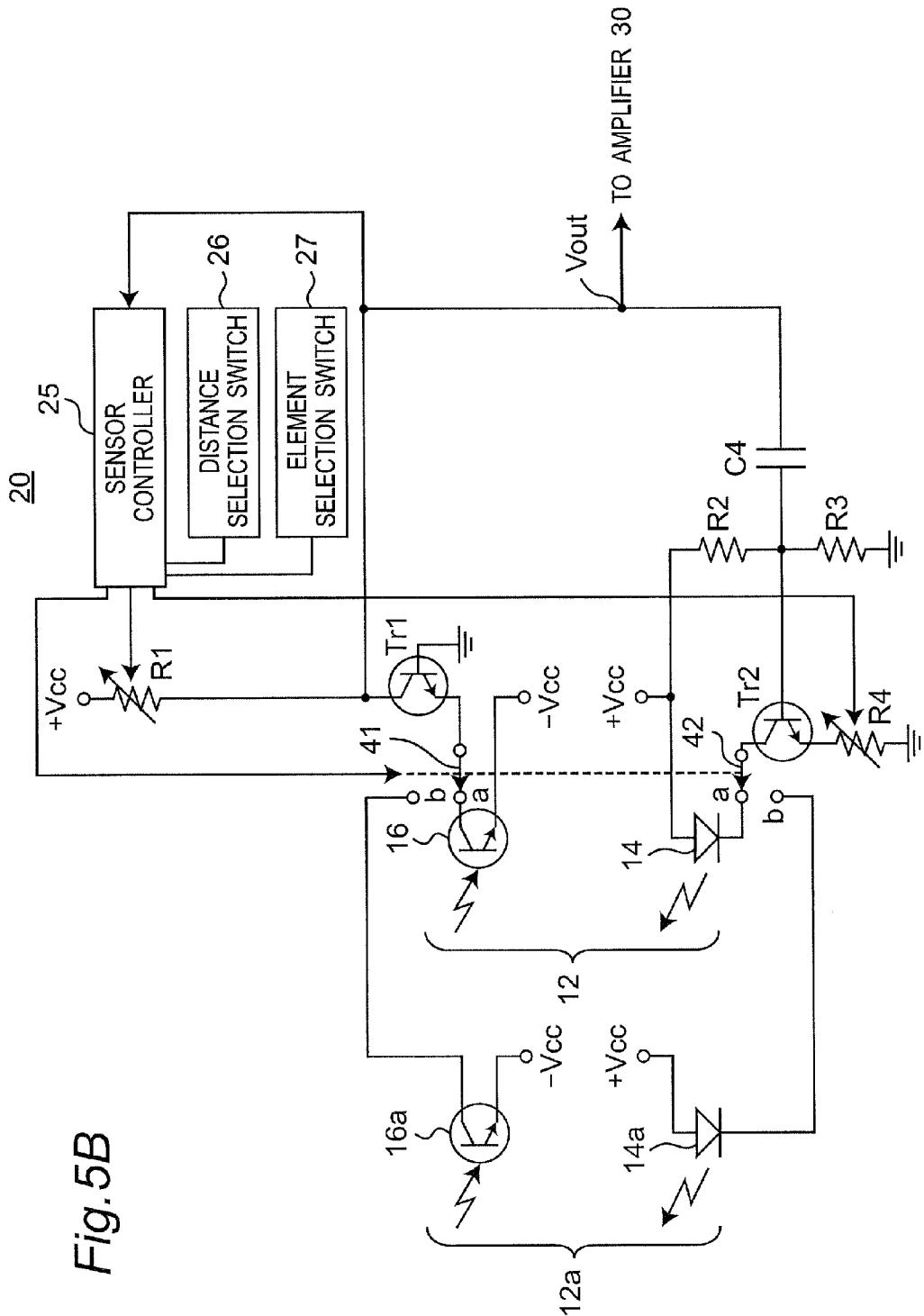
FIG. 5B is a circuit diagram showing a modified embodiment of the optical probe circuit 20 of FIG. 5A.

FIG. 5B is a circuit diagram showing a modified embodiment of the optical probe circuit 20 of FIG. 5A. Although in the optical probe circuit 20 of FIGS. 5A and 5B, only a single pair of the light emitting element 14 and the light receiving element 16 is shown, the optical probe circuit 20 is preferably configured such that the optical probe circuit 20 includes two or more pairs having different boundary propagation distances (a propagation distance at which an output collector current of the light receiving element 16 substantially reaches the maximum thereof), and switching therebetween is performed using an element selection switch 27. This is because, as will be described in detail later with reference to FIGS. 10 to 13, a change in output voltage with respect to a change in propagation distance becomes small near the above-described boundary propagation distance and thus a pulse wave voltage, which is a self-oscillation signal cannot be substantially obtained. Therefore, by the optical probe circuit 20 including two or more pairs of light emitting and receiving sensors having different boundary propagation distances, an unmeasurable propagation distance can be eliminated.

Referring to FIG. 5B, the optical probe circuit 20 includes two pairs of light emitting and receiving sensors including a first optical probe 12 having a light emitting element 14 and a light receiving element 16; and a second optical probe 12a having a light emitting element 14a and a light receiving element 16a, and a sensor controller 25 further includes the element selection switch 27. The element selection switch 27 is configured to be able to select, for example, "element 1" or "element 2". When "element 1" is selected, the sensor controller 25 simultaneously switches the switches 41 and 42 over to the contact "a" side to select the first optical probe 12 having the light emitting element 14 and the light receiving element 16 to allow the first optical probe 12 to operate. When "element 2" is selected, the sensor controller 25 simultaneously switches the switches 41 and 42 over to the contact "b" side to select the second optical probe 12a having the light emitting element 14a and the light receiving element 16a to allow the second optical probe 12a to operate.

FIG. 6A is a front view showing an example of attachment of the light emitting and receiving sensor of the optical probe circuit 20 to the radial artery portion 7 at the wrist of the person to be measured, and FIG. 6B is a front view showing an example of attachment of the light emitting and receiving sensor of the optical probe circuit 20 to a fingertip 9 of the person to be measured.

Figure 7B:
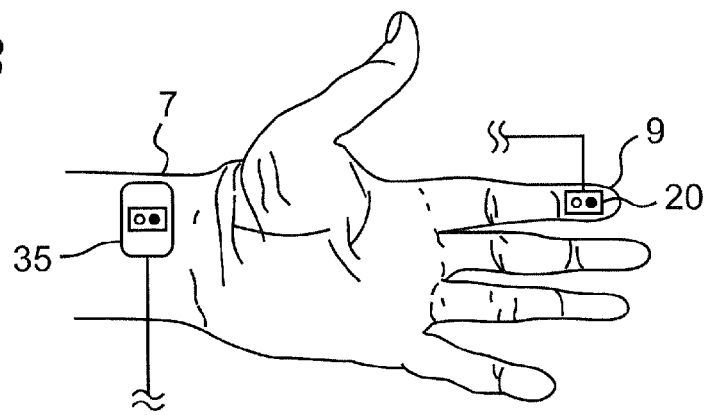
FIG. 7B is a front view showing an example of the case in which a light emitting and receiving sensor of the optical probe circuit 20 is attached to the fingertip 9 of the person to be measured and a pressure sheet sensor 35 is attached to the radial artery portion 7 at the wrist, which is a second modified embodiment.

FIG. 7A is a front view showing exemplary attachment of an optical probe circuit 20A including a pressure sheet sensor and a light emitting and receiving sensor, according to a first modified embodiment and FIG. 7B is a front view showing an example of the case in which a light emitting and receiving sensor of the optical probe circuit 20 is attached to a fingertip 9 of the person to be measured and the pressure sheet sensor 35 is attached to the radial artery portion 7 at the wrist, which is a second modified embodiment. Namely, as shown in FIG. 7A, the pressure sheet sensor may be included in the optical probe circuit 20A together with the light emitting and receiving sensor, or as shown in FIG. 7B, the pressure sheet sensor and the light emitting and receiving sensor may be provided separately. In this case, each pressure sheet sensor is used to create a conversion equation (or a conversion table) for associating a voltage value with a blood pressure value, in a blood pressure value calibration process of FIG. 19, which is performed prior to a vessel pulse wave measurement process of FIG. 20.

Figure 8A:
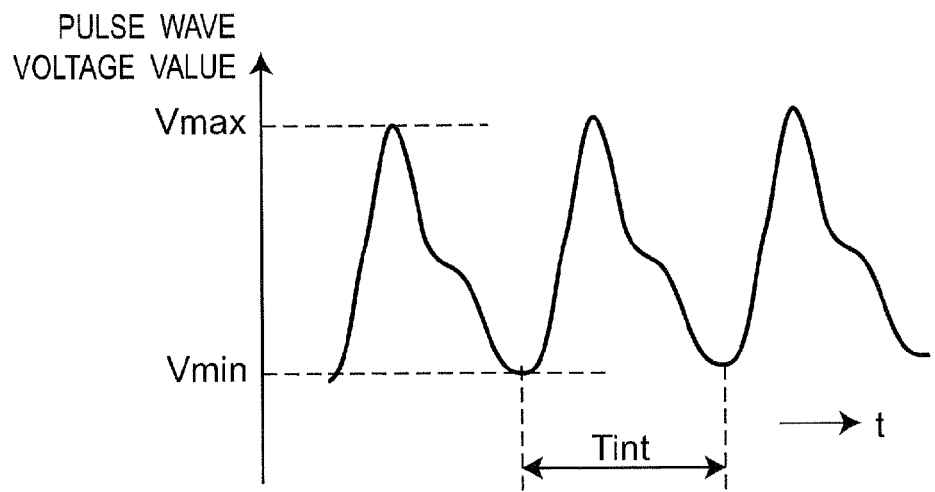
FIG. 8A is a graph showing a maximum voltage value Vmax and a minimum voltage value Vmin of pulse wave voltage values measured by the vessel pulse wave measurement system of FIG. 1.

FIG. 8A is a graph showing a maximum voltage value Vmax and a minimum voltage value Vmin of pulse wave voltage values (for example, output voltage values of the amplifier 30) measured by the vessel pulse wave measurement system of FIG. 1. As is apparent from FIG. 8A, the pulse wave voltage value changes periodically according to a change in pulsation and takes a maximum voltage value Vmax and a minimum voltage value Vmin, and the time interval between two adjacent minimum voltage values Vmin is defined as a time interval Tint.

Figure 8B:
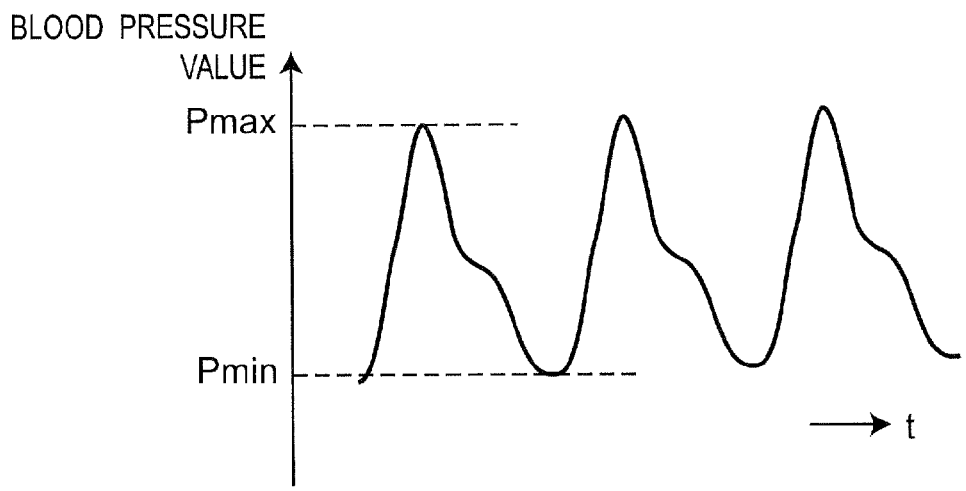
FIG. 8B is a graph showing a maximum blood pressure value Pmax and a minimum blood pressure value Pmin of blood pressure values corresponding to the pulse wave voltage values measured by the vessel pulse wave measurement system of FIG. 1.

FIG. 8B is a graph showing a maximum blood pressure value Pmax and a minimum blood pressure value Pmin of blood pressure values corresponding to the pulse wave voltage values measured by the vessel pulse wave measurement system of FIG. 1. As is apparent from FIG. 8B, the blood pressure value changes periodically according to a change in pulsation in the same manner as the pulse wave voltage value of FIG. 8A, and takes a maximum blood pressure value Pmax and a minimum blood pressure value Pmin. As will be described with reference to FIG. 8C, conversion between FIGS. 8A and 8B can be performed using a conversion equation created in a blood pressure value calibration process of FIG. 19 (a conversion table may be used).

Figure 8C:
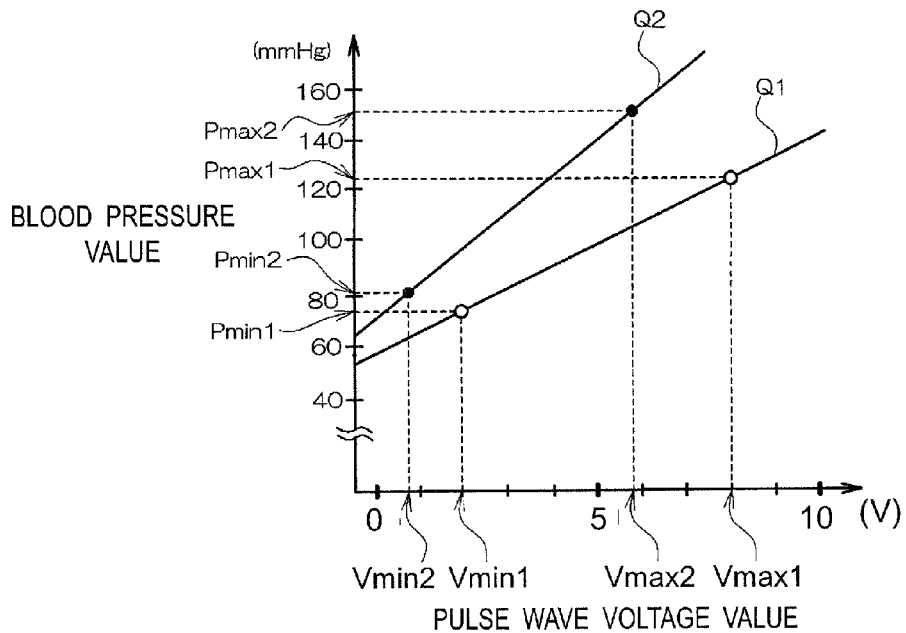
FIG. 8C is a graph showing conversion from pulse wave voltage values measured by the vessel pulse wave measurement system of FIG. 1 to blood pressure values.

FIG. 8C is a graph showing conversion from pulse wave voltage values measured by the vessel pulse wave measurement system of FIG. 1 to blood pressure values. As is known, since different persons to be measured have different correlations between the pulse wave voltage value and the blood pressure value, there is a need to obtain in advance different correlations for different persons to be measured. In addition, even the same person to be measured may have different correlations between the pulse wave voltage value and the blood pressure value, for a resting state and an exercise state, etc., and thus, there is a need to set in advance measurement states and obtain correlations for the respective measurement states. A correlation between the pulse wave voltage value and the blood pressure value obtained by the vessel pulse wave measurement system of FIG. 1 is stored in the internal memory 50m of the apparatus controller 50 in a form of a conversion equation (or a conversion table) for each person to be measured so as to be associated with each measurement condition. FIG. 8C shows that different persons to be measured have different conversion equations Q1 and Q2. By thus performing conversion from a pulse wave voltage value to a blood pressure value, vessel pulse wave measurement such as a pulse rate, a maximum blood pressure Pmax, and a minimum blood pressure Pmin can be performed based on the conversion.

Figure 9A:
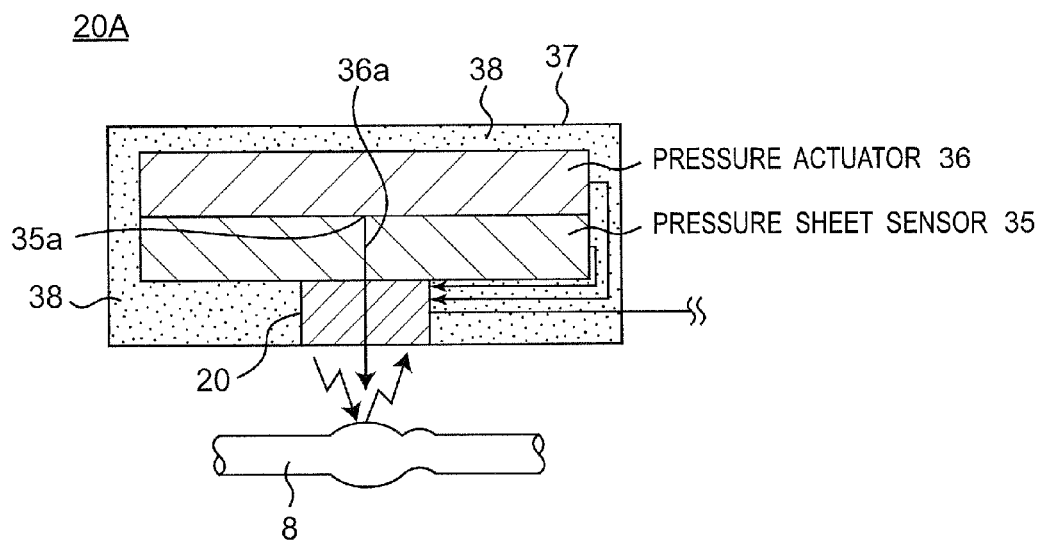
FIG. 9A is a vertical cross-sectional view showing a configuration of the optical probe circuit 20A including a pressure sheet sensor and a light emitting and receiving sensor, according to the first modified embodiment shown in FIG. 7A.

FIG. 9A is a vertical cross-sectional view showing a configuration of the optical probe circuit 20A including a pressure sheet sensor and a light emitting and receiving sensor, according to the first modified embodiment shown in FIG. 7A.

Referring to FIG. 9A, the optical probe circuit 20A has an optical probe circuit 20 including a light emitting element and a light receiving element, a pressure sheet sensor 35 that detects pressure in the blood vessel 8 of the person to be measured, and a pressure actuator 36 that applies pressure to the blood vessel 8 of the person to be measured, which are provided in a predetermined casing 37 using a filling material 38 such as urethane. In this case, it is preferred that the optical probe circuit 20 and the pressure sheet sensor 35 be provided to directly contact with each other and the pressure sheet sensor 35 and the pressure actuator 36 be provided to directly contact with each other. With this, a stress of the pressure actuator 36 is applied in a downward direction 36a shown in the drawing to a pressing portion 35a at the upper center of the pressure sheet sensor 35 and to the optical probe circuit 20 through the pressure sheet sensor 35, and further, the stress is applied to the blood vessel 8 through the skin of the person to be measured from the optical probe circuit 20. The optical probe circuit 20A is used in, for example, a blood pressure value calibration process of FIG. 19.

Figure 9B:
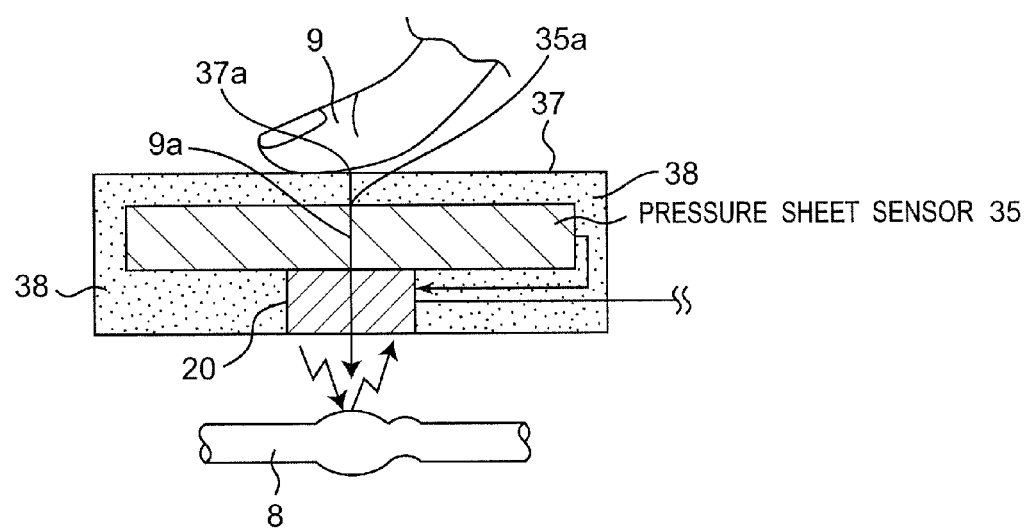
FIG. 9B is a vertical cross-sectional view showing a configuration of an optical probe circuit 20B to be pressed with a fingertip of a human such as a person to be measured, which is a modified embodiment of FIG. 9A.

FIG. 9B is a vertical cross-sectional view showing a configuration of an optical probe circuit 20B to be pressed with a fingertip of a human such as a person to be measured, which is a modified embodiment of FIG. 9A. Instead of the pressure actuator 36 of the optical probe circuit 20A of FIG. 9A, a stress is applied in a downward direction 9a shown in the drawing to a pressing portion 35a at the upper center of a pressure sheet sensor 35 from an upper central portion 37a of a casing 37, with a fingertip 8 of a human such as a person to be measured. The optical probe circuit 20B is used in, for example, a modified embodiment of a blood pressure value calibration process of FIG. 19.

Next, experimental results from which significance for performing a light emitting and receiving sensor control process (FIG. 18) by the sensor controller 25 of FIGS. 5A and 5B is found will be described below. A light emitting and receiving sensor used in the following experiments is an RPR-220 reflective type photo-sensor (photo-reflector) manufactured by ROHM Co., Ltd., and a boundary propagation distance at which the collector current of the output transistor substantially reaches the maximum thereof is 6 to 7 mm. It is noted that, though not shown in the drawings, each of various types of light emitting and receiving sensors has different boundary propagation distances for different applications, and thus, in the present embodiment, it is preferred as described above that a plurality of pairs of light emitting and receiving sensors be provided to eliminate an unmeasurable propagation distance at vessel pulse wave measurement.

FIG. 10 is a graph showing the output voltage with respect to the propagation distance of light for the power supply voltage Vcc=15 V and the resistor R1=18 kΩ and when the resistor R4 is changed in the optical probe circuit 20 of FIGS. 5A and 5B. As is apparent from FIG. 10, near a propagation distance of 6 mm, the output voltage curves have a small gradient and have a small change with respect to the propagation distance, and thus, it can be said that even if the blood vessel wall changes, a change in output voltage is small. In particular, at the resistor R4=200Ω, the gradient of the output voltage is almost zero, and thus it is considered that a change in pulse wave signal cannot be obtained. This is the above-described unmeasurable propagation distance at vessel pulse wave measurement. In order to solve this problem, the unmeasurable propagation distance at vessel pulse wave measurement can be eliminated using light emitting and receiving sensors having different boundary propagation distances.

When the attachment location of the optical probe 12 is a fingertip, the propagation distance is on the order of 0 mm to 2 mm. Thus, it is considered that by allowing the optical probe circuit 20 to operate in a region of the output voltage curves on the left side of a boundary propagation distance (6 mm), a change in pulse wave signal can be obtained. On the other hand, when the attachment location of the optical probe 12 is a radial artery portion at the wrist, the propagation distance is on the order of 1 mm to 3 mm. Thus, it is considered that by allowing the optical probe circuit 20 to operate in a region of the output voltage curves on the right side of the boundary propagation distance (6 mm) corresponding to a minimal value of the output voltage curves, a change in pulse wave signal can be obtained. Therefore, the former can be set as an initial value of an operating point for "small distance" and the latter can be set as an initial value of an operating point for "large distance". In addition, it is considered that by changing the resistor R4, the gradient of an output voltage curve can be increased, enabling to obtain a larger change in pulse wave signal.

The setting of an initial value of an operating point will be described below with reference to a specific example of FIG. 10. When the resistor R4=250Ω, by allowing the optical probe circuit 20 to operate at an operating point P1 at the propagation distance in the "small distance" region=4 mm, a gradient angle θ1 greater than or equal to a predetermined threshold value can be obtained. After setting this as the initial value of the operating point, the sensor controller 25 performs control to change the resistance values of the resistors R1 and R4 so that a substantially maximum output voltage value Vout can be obtained. With this, a larger pulse wave signal can be obtained. In addition, when the resistor R4=250Ω, by allowing the optical probe circuit 20 to operate at an operating point P2 at the propagation distance in the "large distance" region=10 mm, a gradient angle θ2 greater than or equal to the predetermined threshold value can be obtained. After setting this as the initial value of the operating point, the sensor controller 25 performs control to change the resistance values of the resistors R1 and R4 so that a substantially maximum output voltage value Vout (self-oscillation signal) can be obtained. With this, a larger pulse wave signal can be obtained.

It is noted that in the present embodiment, the operating point of the drive circuit is determined, for example, by the resistance value of the resistor R4 and the operating point of the detection circuit is determined by, for example, the resistance value of the resistor R1. By the determination of the operating point of the drive circuit and the operating point of the drive circuit, an operating point (for example, P1 or P2) in an electric characteristic of FIG. 10 can be determined.

Figure 11:
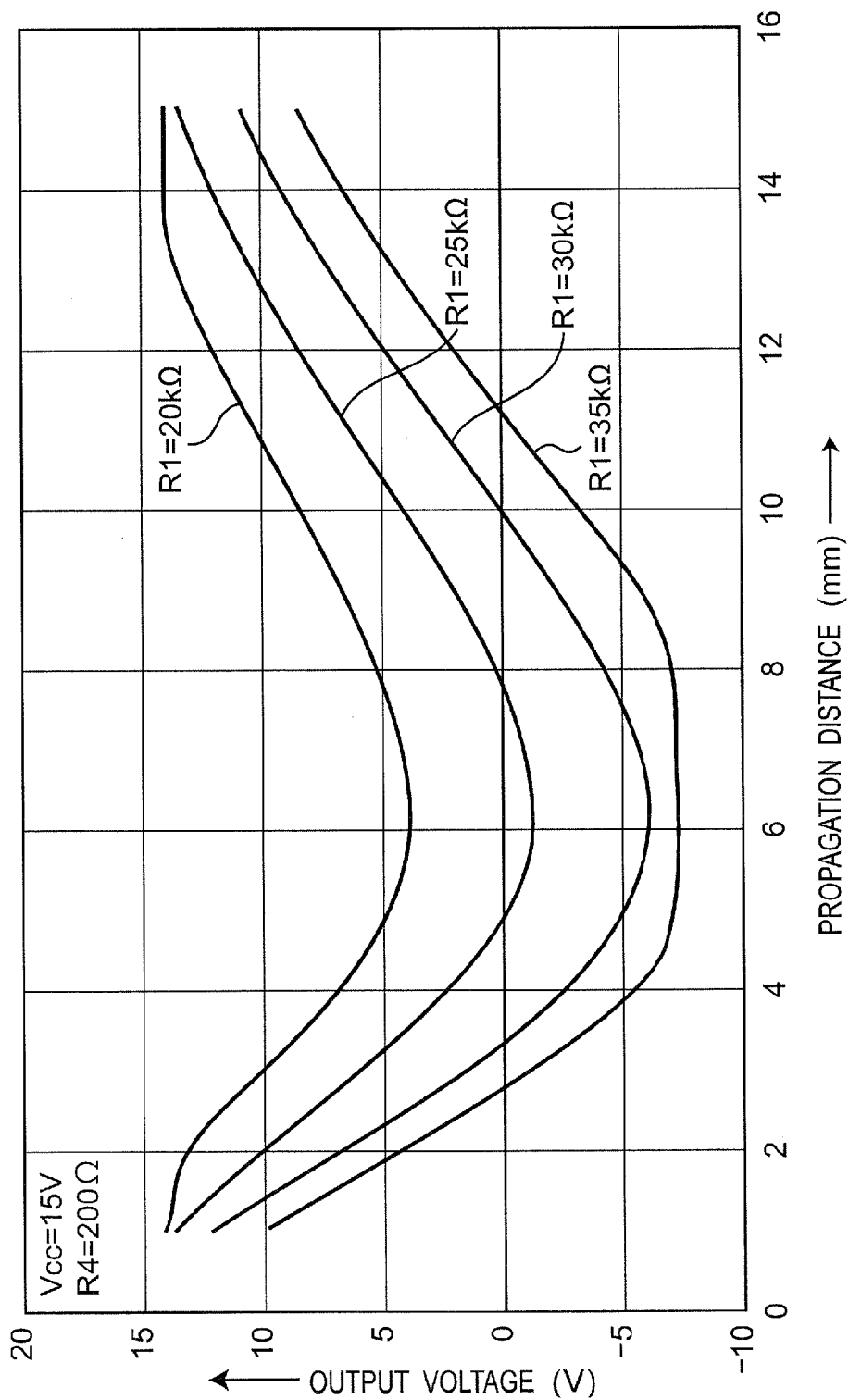
FIG. 11 is a graph showing output voltage with respect to the propagation distance of light for the power supply voltage Vcc=15 V and the resistor R4=200Ω and when the resistor R1 is changed in the optical probe circuit 20 of FIGS. 5A and 5B.

FIG. 11 is a graph showing the output voltage with respect to the propagation distance of light for the power supply voltage Vcc=15 V and the resistor R4=200Ω and when the resistor R1 is changed in the optical probe circuit 20 of FIGS. 5A and 5B. The output voltage curves of FIG. 11 which are similar to the output voltage curves of FIG. 10 are obtained, and the setting of initial values of operating points for "large distance" and "small distance" and control of the gradient of an output voltage curve by a change of resistor R1 and the setting for maximization thereof can be performed.

Figure 12:
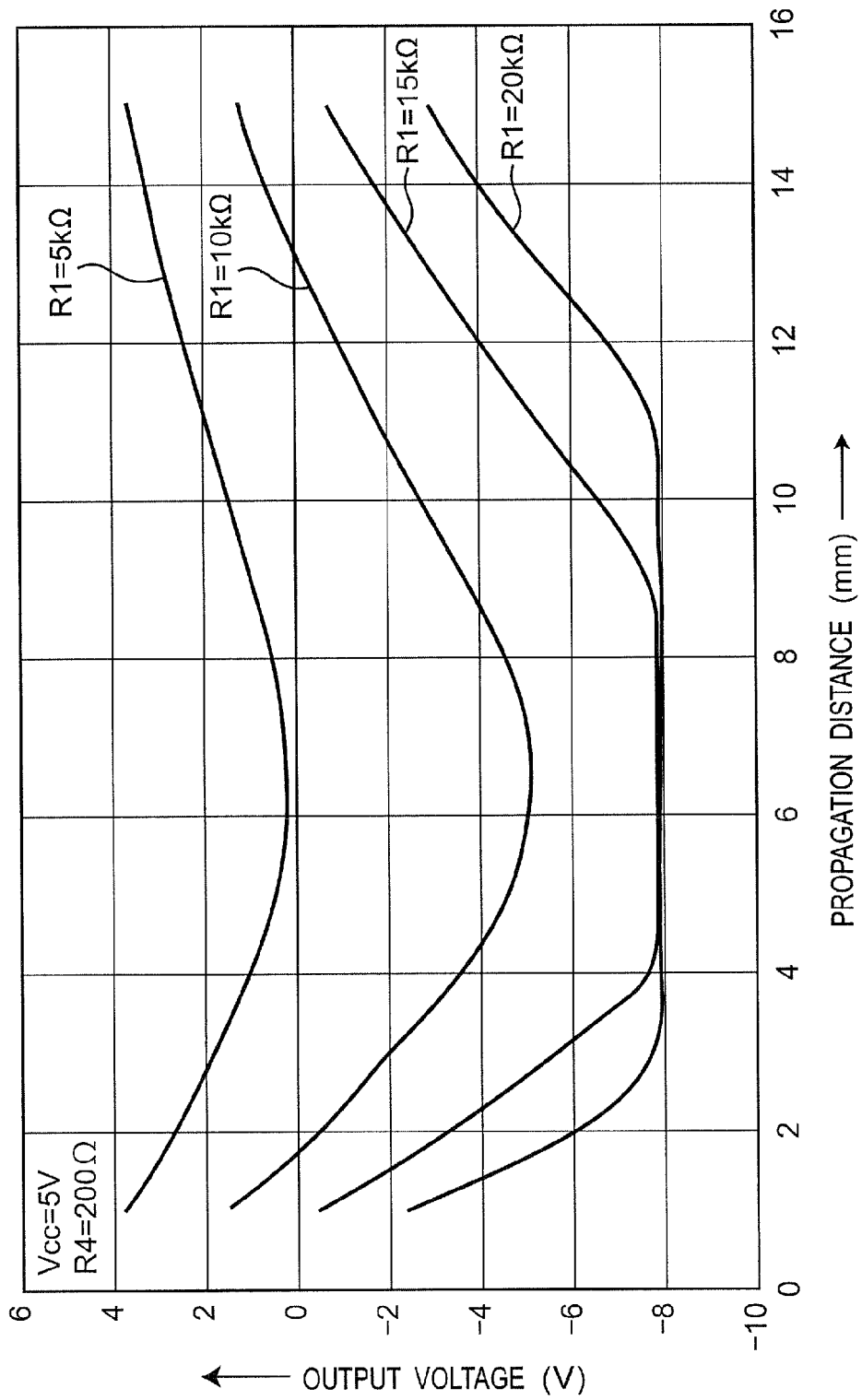
FIG. 12 is a graph showing output voltage with respect to the propagation distance of light for the power supply voltage Vcc=5 V and the resistor R4=200Ω and when the resistor R1 is changed in the optical probe circuit 20 of FIGS. 5A and 5B.

FIG. 12 is a graph showing the output voltage with respect to the propagation distance of light for the power supply voltage Vcc=5 V and the resistor R4=200Ω and when the resistor R1 is changed in the optical probe circuit 20 of FIGS. 5A and 5B. The output voltage curves of FIG. 12 which are similar to the output voltage curves of FIG. 11 are obtained excluding a saturation state in a longer distance range at the resistor R1=15 kΩ and 20 kΩ, and the setting of initial values of operating points for "large distance" and "small distance" and control of the gradient of an output voltage curve by a change of resistor R1 and the setting for maximization thereof can be performed.

Figure 13:
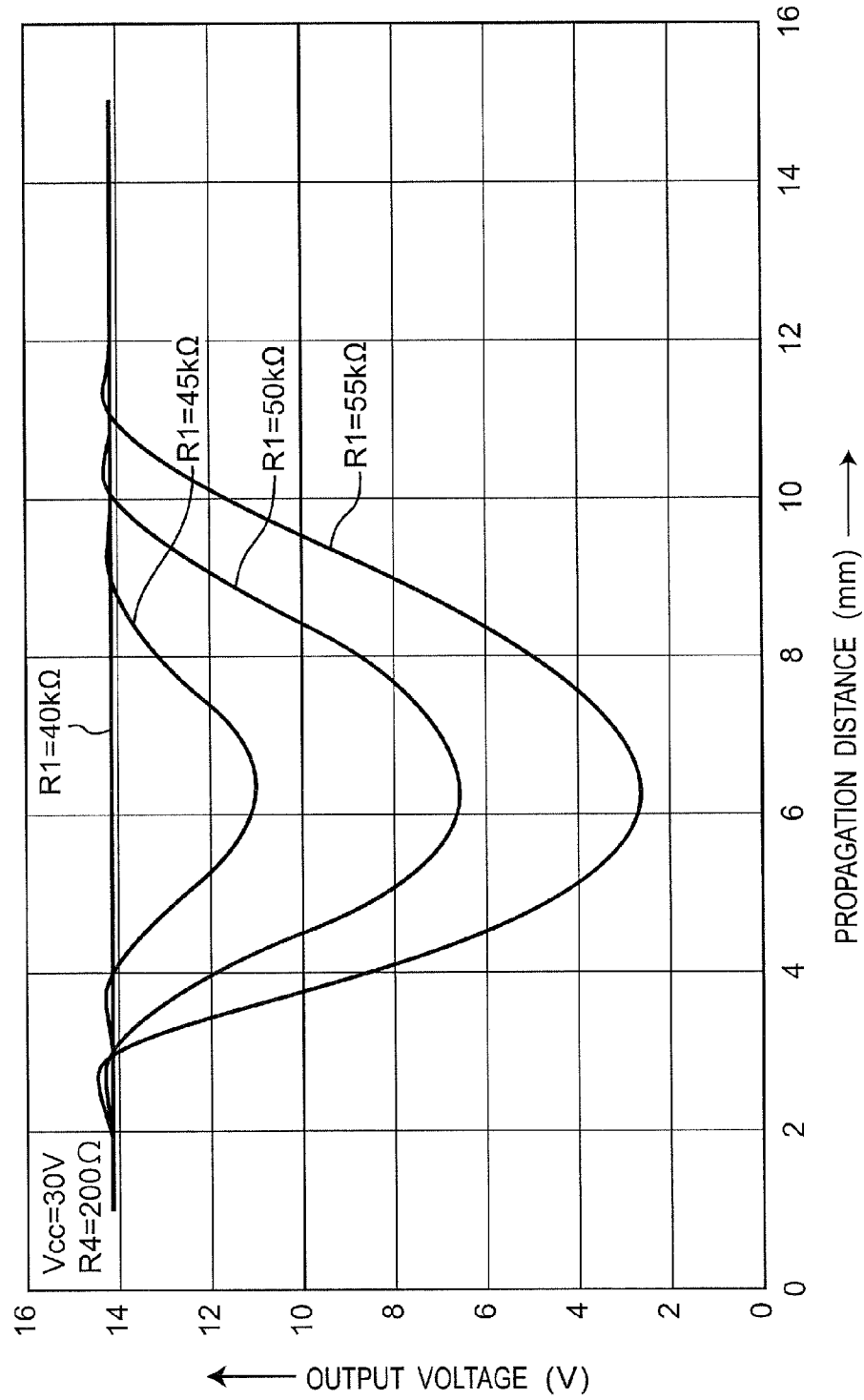
FIG. 13 is a graph showing output voltage with respect to the propagation distance of light for the power supply voltage Vcc=30 V and the resistor R4=200Ω and when the resistor R1 is changed in the optical probe circuit 20 of FIGS. 5A and 5B.

FIG. 13 is a graph showing the output voltage with respect to the propagation distance of light for the power supply voltage Vcc=30 V and the resistor R4=200Ω and when the resistor R1 is changed in the optical probe circuit 20 of FIGS. 5A and 5B. The output voltage curves of FIG. 13 which are similar to the output voltage curves of FIG. 11 are obtained excluding a zero gradient state in a longer distance range at the resistor R1=40 kΩ, and the setting of initial values of operating points for "large distance" and "small distance" and control of the gradient of an output voltage curve by a change of resistor R1 and the setting for maximization thereof can be performed.

It is noted that, though a graph is not shown, when the light emitting element and the light receiving element of the optical probe 12 are replaced with another pair of elements; the boundary propagation distance can be made different. With this, the distance ranges for the above-described so-called "large distance" and "small distance" can be made different. Namely, distance range selection setting can be selected by the element selection switch 27.

As described above, the sensor controller 25 includes the distance selection switch 26 and preferably further includes the element selection switch 27, and can select, for example, "large distance" or "small distance" by the distance selection switch 26 to set an initial value that determines the operating point of the optical probe circuit 20 including the drive circuit and the detection circuit (specifically, the initial values of the resistors R1 and R4), and can select, for example, "element 1" or "element 2" by the element selection switch 27. According to a light emitting and receiving sensor control process of FIG. 18, the sensor controller 25 sets predetermined initial values for the resistors R1 and R4 (which means values corresponding to optimal operating points determined based on the characteristics of output voltage with respect to propagation distance measured in advance), and then performs control to change the resistance values of the resistors R1 and R4 such that an output voltage Vout of the optical probe circuit 20 substantially reaches the maximum thereof.

Figure 14:
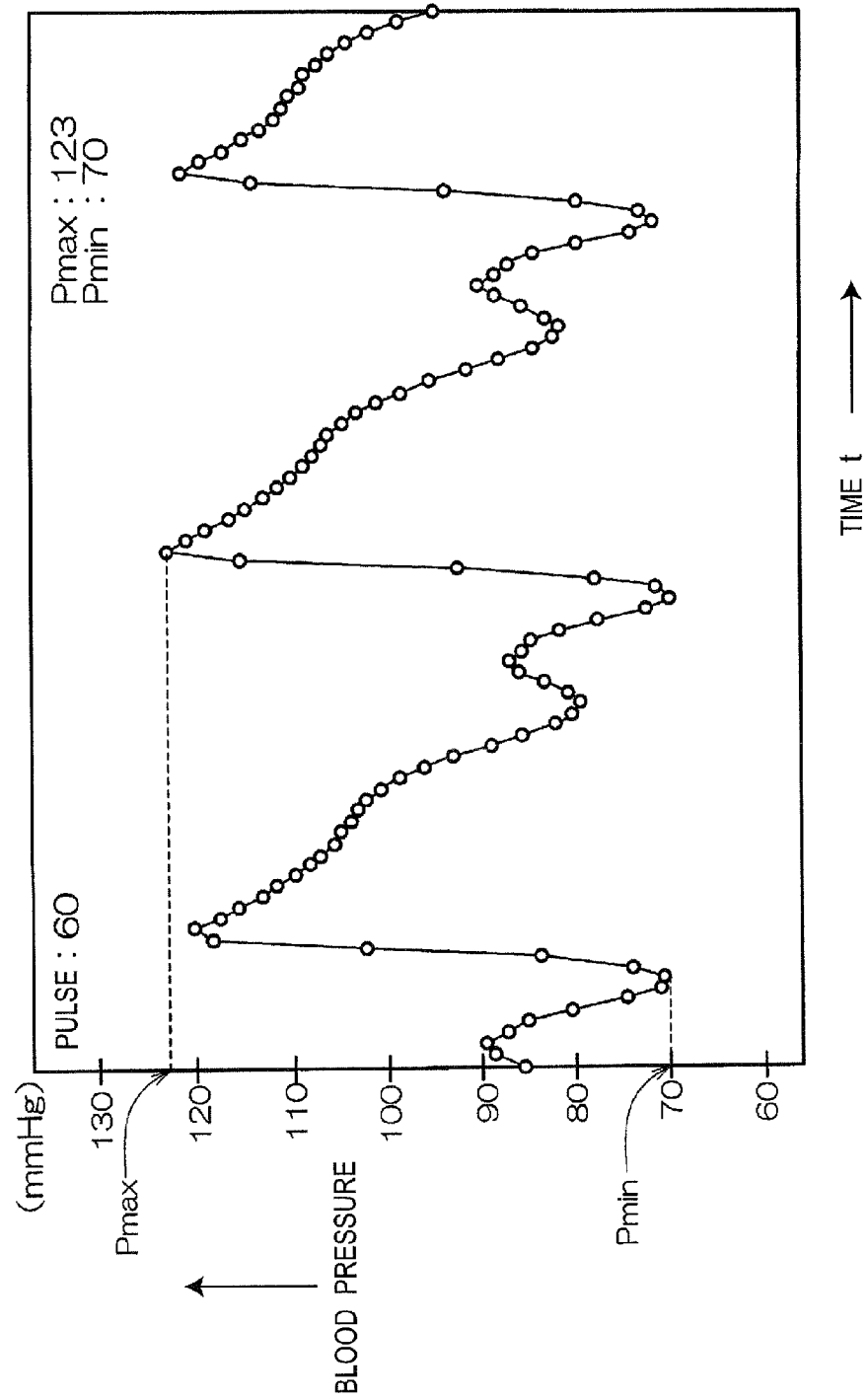
FIG. 14 is a graph showing a blood pressure waveform into which a pulsation waveform measured by the vessel pulse wave measurement system of FIG. 1 is converted.

FIG. 14 is a graph showing a blood pressure waveform to which a pulsation waveform measured by the vessel pulse wave measurement system of FIG. 1 is converted. As is apparent from FIG. 14, by converting an output voltage waveform of the pulsation waveform to a blood pressure waveform, display of a pulse wave waveform of FIG. 14 can be obtained.

Figure 15A:
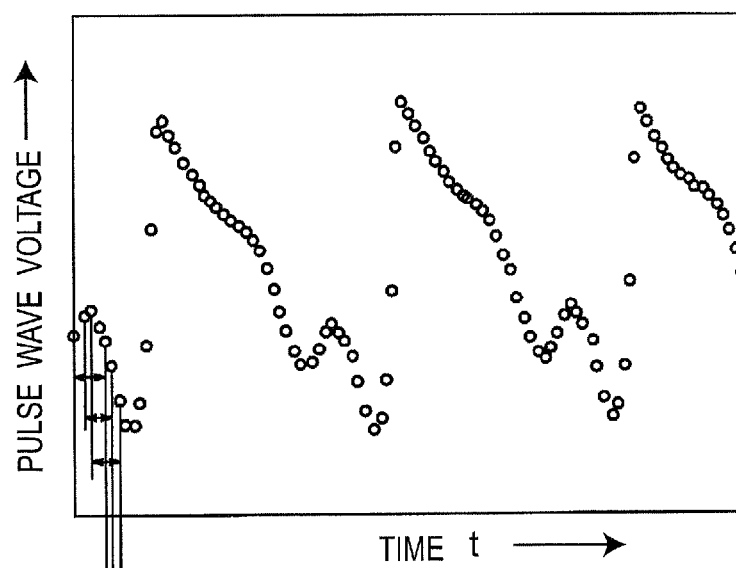
FIG. 15A is a graph showing a pulse wave voltage in an operation of processing a pulsation waveform using a moving average method in the vessel pulse wave measurement system of FIG. 1.
Figure 15B:
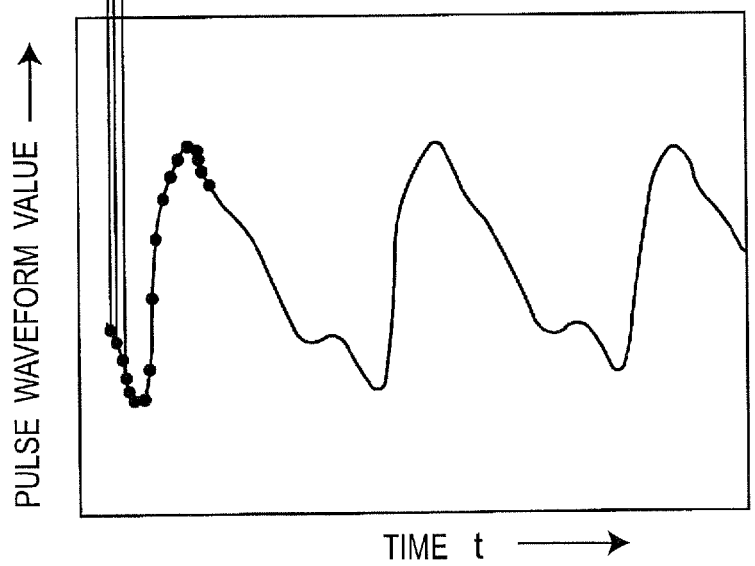
FIG. 15B is a graph showing a pulse waveform value in the operation of FIG. 15A.

FIG. 15A is a graph showing a pulse wave voltage in an operation of processing a pulsation waveform using a moving average method in the vessel pulse wave measurement system of FIG. 1, and FIG. 15B is a graph showing a pulse waveform value in the operation of FIG. 15A. FIGS. 15A and 15B are graphs showing a state in which a smooth pulsation waveform is created using a moving average method from raw data on a pulse wave voltage obtained by the vessel pulse wave measurement system. In FIG. 15A, the horizontal axis represents time and the vertical axis represents pulse wave voltage, and a state of a change in pulse wave voltage at each sampling time is shown. In FIG. 15B, the horizontal axis represents time, and the starting point location thereof, etc., coincide with those in FIG. 15A. The vertical axis represents a moving average value "b" of data for each sampling time in FIG. 15A. A moving average value is performed for, for example, five pieces of data. In this case, when raw data on a pulse wave voltage for a sampling time "i" is "$a_i$", a moving average value "$b_i$" for the sampling time "i" can be computed using the following equation:

$$b=(a_{i-4}+a_{i-3}+a_{i-2}+a_{i-1}+a_i)/5.$$

Namely, when sampling data "$a_i$" is obtained, a moving average value "$b_i$" can be calculated immediately, and thus, a real-time process can be performed. It is noted that the number of pieces of data used for moving average is not limited to five.

Figure 16A:
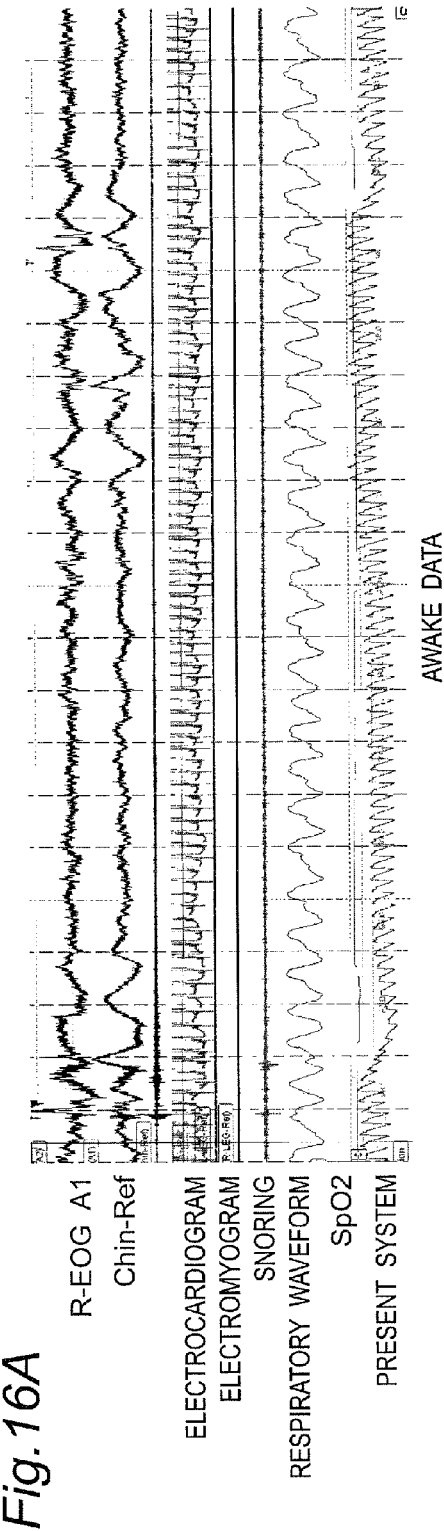
FIG. 16A is a graph showing an example of various types of signal waveforms when a certain person to be measured is awake, which are measured by the vessel pulse wave measurement system of FIG. 1.
Figure 16B:
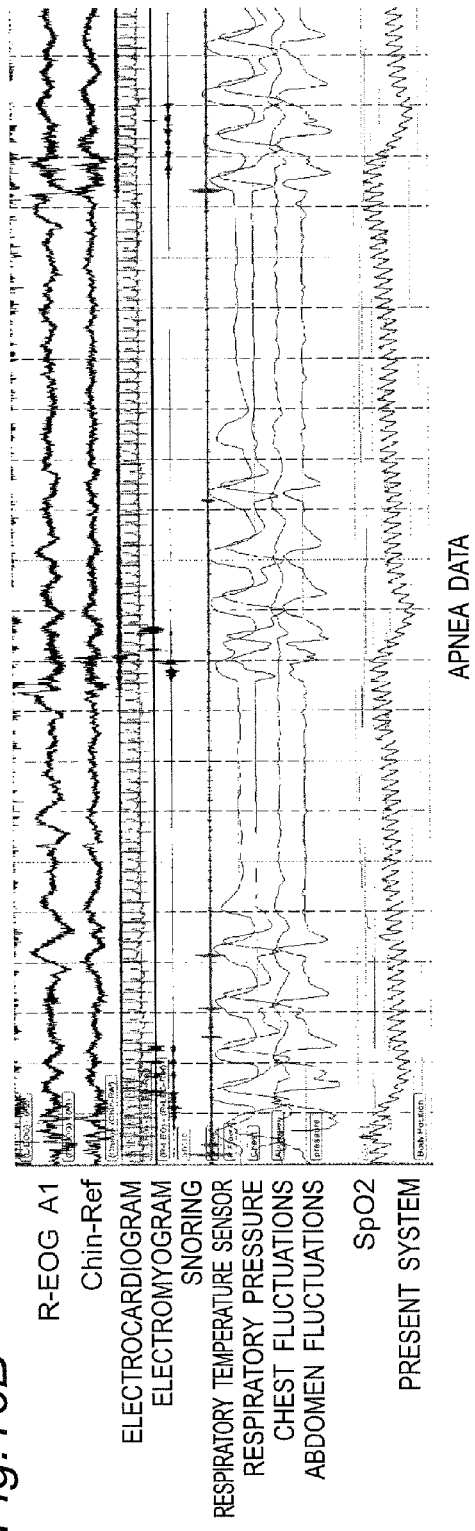
FIG. 16B is a graph showing an example of various types of signal waveforms when the certain person to be measured has apnea which are measured by the vessel pulse wave measurement system of FIG. 1.

FIG. 16A is a graph showing an example of various types of signal waveforms when a certain person to be measured is awake which are measured by the vessel pulse wave measurement system of FIG. 1, and FIG. 16B is a graph showing an example of various types of signal waveforms when the certain person to be measured has apnea which are measured by the vessel pulse wave measurement system of FIG. 1.

In FIG. 16A, various kinds of measured waveforms in case of awake state are shown as follows:

(a) R-EOG A1: an ocular waveform measured by a well-known electrooculograph.

(b) Chin-Ref: the amount of displacement of the chin measured by a well-known chin movement measuring apparatus.

(c) Electrocardiogram: a cardiac waveform measured by a well-known electrocardiograph.

(d) Electromyogram: an electromyographic waveform measured by a well-known electromyograph.

(e) Snoring: a snoring sound measured by a small microphone.

(f) Respiratory waveform: a respiratory waveform obtained when a pressure-sensitive sensor detects a change in pressure under the body along with the respiration of the person to be measured and a respiratory waveform is measured.

(g) SpO2: blood oxygen saturation level measured by a well-known pulse oximeter.

(h) Present system: a pulse waveform measured by the vessel pulse wave measurement system according to the present embodiment.

In FIG. 16B, various kind of measured waveforms when apnea occurs are shown as follows:

(a) R-EOG A1: an ocular waveform measured by a well-known electrooculograph.

(b) Chin-Ref: the amount of displacement of the chin measured by a well-known chin movement measuring apparatus.

(c) Electrocardiogram: a cardiac waveform measured by a well-known electrocardiograph.

(d) Electromyogram: an electromyographic waveform measured by a well-known electromyograph.

(e) Snoring: a snoring sound measured by a small microphone.

(f) Respiratory temperature sensor: respiratory temperature measured by a temperature sensor provided in the mouth.

(g) Respiratory pressure: a respiratory pressure waveform obtained when a pressure-sensitive sensor detects a change in pressure under the body along with the respiration of the person to be measured and a respiratory waveform is measured.

(h) Chest Fluctuations: the amount of fluctuation in the chest measured by a stress sensor that measures a change in the chest of the person to be measured.

(i) Abdomen Fluctuations: the amount of fluctuation in the abdomen measured by a stress sensor that measures a change in the abdomen of the person to be measured.

(j) SpO2: blood oxygen saturation level measured by a well-known pulse oximeter.

(k) Present system: a pulse waveform measured by the vessel pulse wave measurement system according to the present embodiment.

The data of FIGS. 16A and 16B measured by the vessel pulse wave measurement system according to the present embodiment includes a lot of pieces of information that is not obtained by measuring apparatuses available up to now.

Referring to FIG. 16A, although the person to be measured is in normal REM sleep, there are two awake reactions during the 120-second recording, and at each of the two awake reactions the pulse pressure slightly rises when the awake reaction begins and then exhibits a sudden drop. An increase in sympathetic activity and a temporary increase in peripheral vascular resistance due to the awake reaction and a subsequent drop in pulse pressure due to reflex vasodilatation are observed. Thus, it is considered that a change in pulse pressure during normal sleep is synchronized with an awake reaction on the brain waves. With this, it is considered that a sleep evaluation can be performed in the small vessel pulse wave measurement system which does not measure brain waves.

Referring to FIG. 16B, it can be seen that in a series of typical apnea, labored respiration to an awake reaction, and hyperventilation, the pulse pressure gradually rises until the end of the apnea while fluctuations in small cycles that are synchronized with the labored respiration during the apnea are observed (it is considered that a frequency analysis needs to be performed from a measured constant because the fluctuations are small). Thereafter, the pulse pressure suddenly drops with an awake reaction and resumption of respiration to hyperventilation. Probably, the blood pressure of this patient upon resting during the daytime is at a stable level after the drop, and the rise in blood pressure during the apnea is caused by an excessive increase in sympathetic activity due to the apnea. In the past studies conducted by the inventors, there is even a patient having a peak systolic blood pressure of 228. Therefore, it is considered that special circulatory dynamics during sleep can be evaluated which relate to the development of circulatory problems where the frequency of complications is problematic in the case of a patient with apnea syndrome.

From the graphs of pulse waveforms of FIGS. 16A and 16B, it can be seen that, when REM awake, the maximum blood pressure value Pmax increases moderately as compared with when apnea occurs and then decreases, which is repeated. In addition, it can be seen that, when apnea occurs, the maximum blood pressure value Pmax increases more rapidly as compared with when REM awake and then decreases, which is repeated.

Figure 17A:
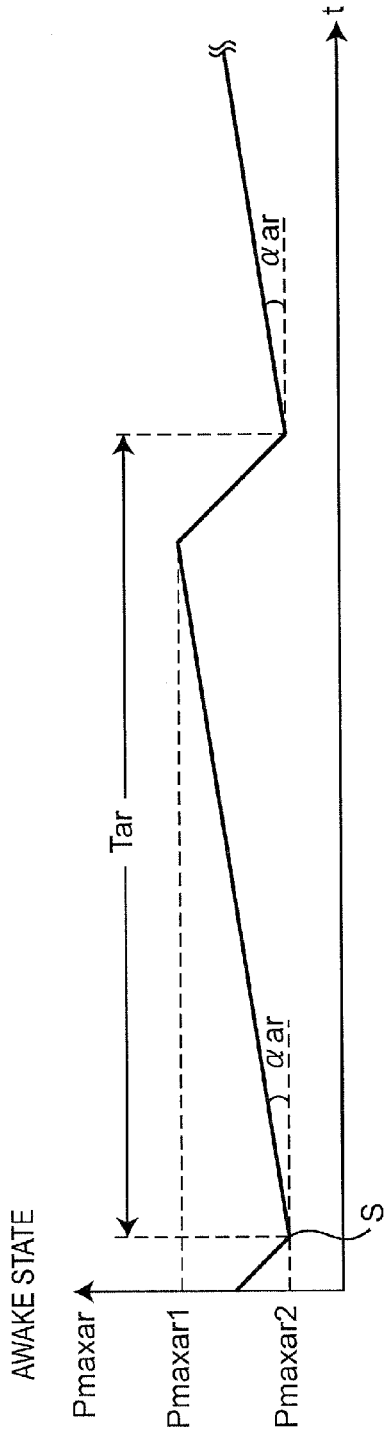
FIG. 17A is a diagram showing modeled changes in maximum blood pressure value Pmax in case of awake state.
Figure 17B:
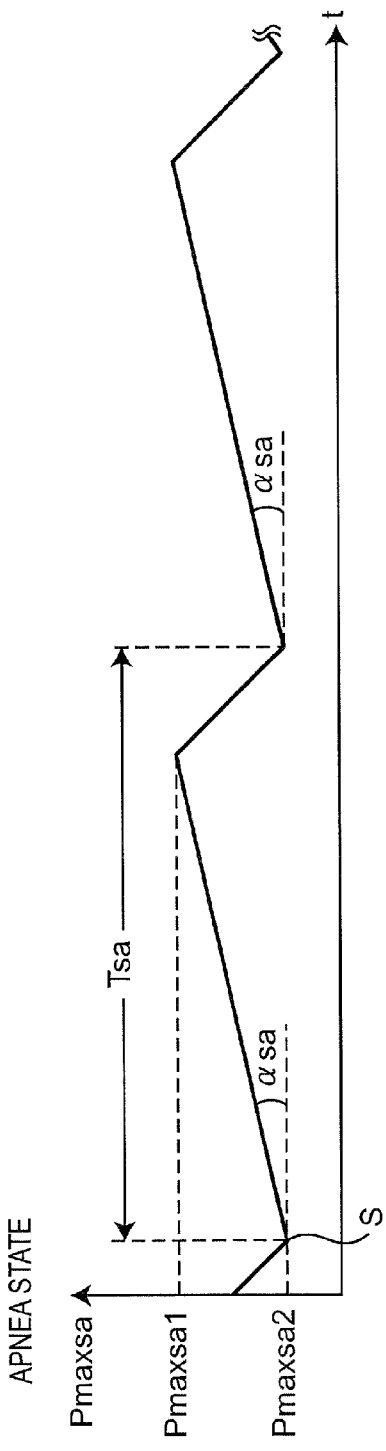
FIG. 17B is a diagram showing modeled changes in maximum blood pressure value Pmax in case of apnea state.

FIG. 17A is a diagram showing modeled changes in maximum blood pressure value Pmax in case of awake state, and FIG. 17B is a diagram showing modeled changes in maximum blood pressure value Pmax in case of apnea state. As is apparent from the model diagrams of the maximum blood pressure value Pmax of FIGS. 17A and 17B, it can be seen that a change cycle Tar of the maximum blood pressure value Pmax in case of REM awake state is longer than that in case of apnea state, and an increase gradient angle αar of the maximum blood pressure value Pmax in case of REM awake state, which is viewed from a starting point S is smaller than that in case of apnea state. Based on these findings and clinical trials, a flowchart of a sleep state determination process of FIG. 21 is created.

FIG. 18 is a flowchart showing a light emitting and receiving sensor control process, which is performed by the sensor controller 25 of FIGS. 5A and 5B. In the light emitting and receiving sensor control process, the case of FIG. 5B according to the modified embodiment including the embodiment of FIGS. 5A and 5B will be described.

Referring to FIG. 18, first of all, in step S1, it is determined whether the set values of the selection switches 26 and 27 are "large distance" and "element 1". If YES, then the control flow proceeds to step S4. On the other hand, if NO, then the control flow proceeds to step S2. Then, in step S2, it is determined whether the set values of the selection switches 26 and 27 are "small distance" and "element 1". If YES, then the control flow proceeds to step S5. On the other hand, if NO, then the control flow proceeds to step S3. Further, in step S3, it is determined whether the set values of the selection switches 26 and 27 are "large distance" and "element 2". If YES, then the control flow proceeds to step S6. On the other hand, if NO, then the control flow proceeds to step S7.

In step S4, the resistance values R1int1 and R4int1 of the resistors R1 and R4 which are the initial values of optimal operating points for "large distance" and "element 1" are set as the resistance values of the resistors R1 and R4, respectively, and the control flow proceeds to step S8. In step S5, the resistance values R1int2 and R4int2 of the resistors R1 and R4 which are the initial values of optimal operating points for "small distance" and "element 1" are set as the resistance values of the resistors R1 and R4, respectively, and the control flow proceeds to step S8. In step S6, the resistance values R1int3 and R4int3 of the resistors R1 and R4 which are the initial values of optimal operating points for "large distance" and "element 2" are set as the resistance values of the resistors R1 and R4, respectively, and the control flow proceeds to step S8. In step S7, the resistance values R1int4 and R4int4 of the resistors R1 and R4 which are the initial values of optimal operating points for "small distance" and "element 2" are set as the resistance values of the resistors R1 and R4, respectively, and the control flow proceeds to step S8. Further, in step S8, the resistance value of the resistor R4 is changed with the resistance value of the resistor R1 fixed such that the output voltage Vout substantially reaches the maximum thereof. Then, in step S9, the resistance value of the resistor R1 is changed with the resistance value of the resistor R4 fixed such that the output voltage Vout substantially reaches the maximum thereof, and then the process ends.

It is noted that the resistance values R1int1 to R1int4 and R4int1 to R4int4 of the resistors R1 and R4 which are the initial values of the operating points are determined in advance from the electric characteristics of FIG. 10, etc., which is measured in advance, and are stored in the internal memory 50m.

Although, in the above-described process of FIG. 18, after setting predetermined initial values for the operating points of both the detection circuit and the drive circuit, the operating points of both the detection circuit and the drive circuit are controlled such that the output voltage Vout substantially reaches the maximum thereof, the present invention is not limited thereto, and after setting predetermined initial values for the operating points of both the detection circuit and the drive circuit, the operating point of at least one of the detection circuit and the drive circuit may be controlled such that the output voltage Vout substantially reaches the maximum thereof.

Figure 19:
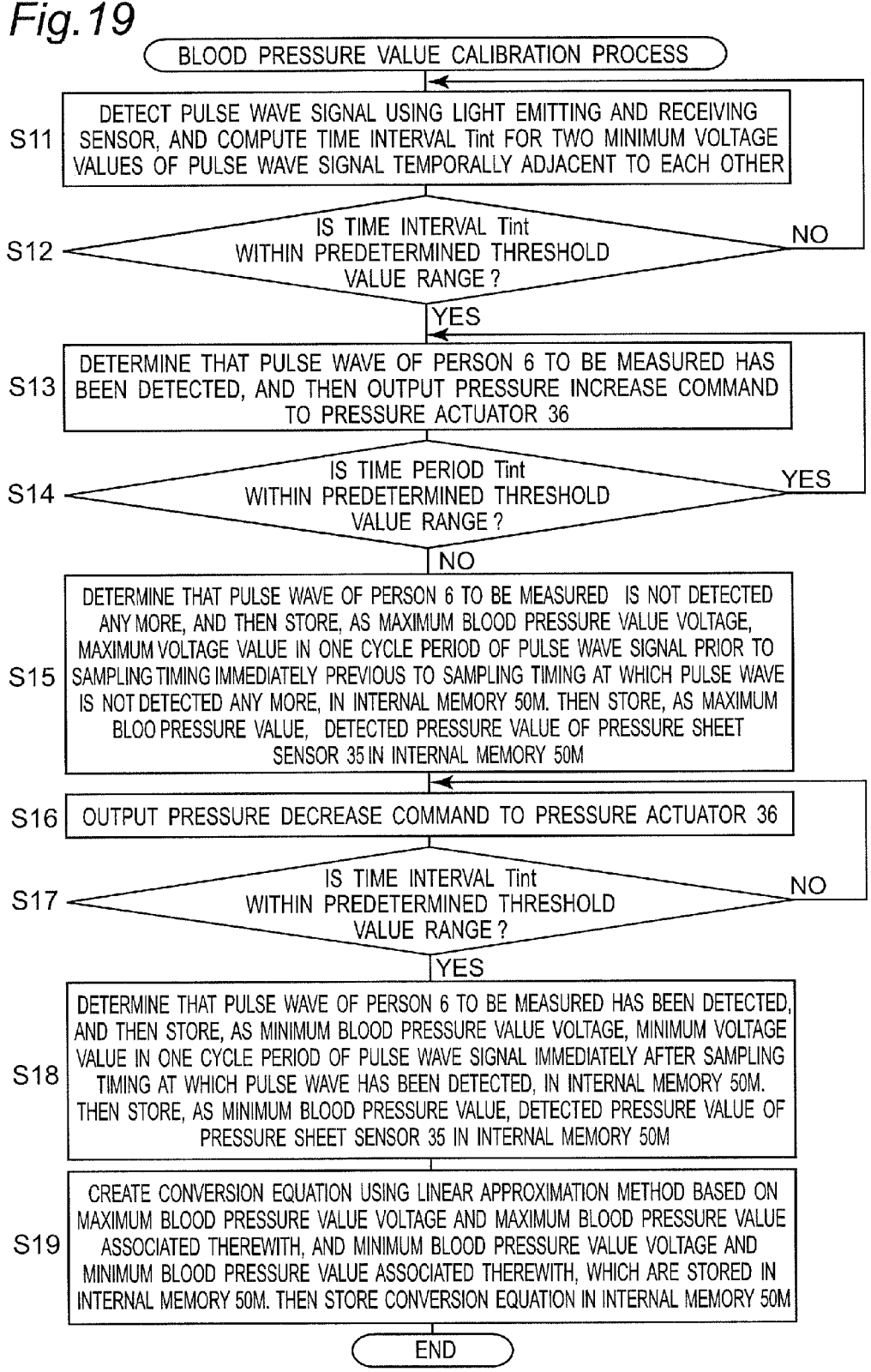
FIG. 19 is a flowchart showing a blood pressure value calibration process, which is performed by a blood pressure value calibration processing module 52 of an apparatus controller 50 of FIG. 1.

FIG. 19 is a flowchart showing a blood pressure value calibration process, which is performed by the blood pressure value calibration processing module 52 of the apparatus controller 50 of FIG. 1 to calibrate the maximum blood pressure value and the minimum blood pressure value using the same principle as the cuff pressure method according to the prior art.

Referring to FIG. 19, first of all, in step S11, a pulse wave signal is detected using the light emitting and receiving sensor, and a time interval Tint for two minimum voltage values of the pulse wave signal temporally adjacent to each other (See FIG. 8A) is computed. In step S12, it is determined whether the time interval Tint is within a predetermined threshold value range (namely, it is determined whether a pulse wave signal is detected). If YES, then the control flow proceeds to step S13. On the other hand, if NO, then the control flow returns to step S11. In this case, the predetermined threshold value range of the time interval Tint is a range to determine whether a pulse wave signal has been detected, and the above-described threshold value range is, as an empirical value, for example, $0.2 \text{ seconds} \leq \text{Tint} \leq 2 \text{ seconds}$. If the time interval Tint is within the threshold value range, then it is determined that a pulse wave has been detected. In step S13, it is determined that a pulse wave of the person 6 to be measured has been detected, and thus, a pressure increase command to increment a predetermined differential pressure is outputted to the pressure actuator 36. Then, in step S14, it is determined whether a time interval Tint is within the predetermined threshold value range (namely, it is determined whether a pulse wave signal is detected). If NO, then the control flow proceeds to step S15. On the other hand, if YES, then the control flow returns to step S13.

In step S15, it is determined that a pulse wave of the person 6 to be measured is not detected any more, and thus, a maximum voltage value in one cycle period of the pulse wave signal prior to sampling timing immediately previous to sampling timing at which a pulse wave is not detected any more is stored in the internal memory 50m as a maximum blood pressure value voltage, and a detected pressure value of the pressure sheet sensor 35 is stored in the internal memory 50m as a maximum blood pressure value. Then, in step S16, a pressure decrease command to decrement a predetermined differential pressure is outputted to the pressure actuator 36. Then, in step S17, it is determined whether a time interval Tint is within the predetermined threshold value range (namely, it is determined whether a pulse wave signal is detected). If YES, then the control flow proceeds to step S18. On the other hand, if NO, then the control flow returns to step S16. In step S18, it is determined that a pulse wave of the person 6 to be measured has been detected, and thus, a minimum voltage value in one cycle period of the pulse wave signal immediately after sampling timing at which the pulse wave has been detected is stored in the internal memory 50m as a minimum blood pressure value voltage, and a detected pressure value of the pressure sheet sensor 35 is stored in the internal memory 50m as a minimum blood pressure value. In addition, in step S19, as described with reference to FIG. 8C, a conversion equation (or a blood pressure conversion table) representing conversion from a voltage value to a blood pressure value is created using a linear approximation method based on the maximum blood pressure value voltage and the maximum blood pressure value corresponding to the maximum blood pressure value voltage, and the minimum blood pressure value voltage and the minimum blood pressure value corresponding to the minimum blood pressure value voltage, which are stored in the internal memory 50m, and the conversion equation is stored in the internal memory 50m, and then the process is completed.

Although the blood pressure value calibration process of FIG. 19 is performed using, for example, the optical probe circuit 20A of FIG. 9A, the present invention is not limited thereto and the blood pressure value calibration process may be performed using the optical probe circuit 20B of FIG. 9B. In this case, in step S13, it is determined that a pulse wave of the person 6 to be measured has been detected, and thus, without using the pressure actuator 36, a message instructing a human such as a person to be measured to press the top of the optical probe circuit 20B (the pressing portion 35a of the pressure sheet sensor 35 through the top) with the fingertip 9 is displayed on an LCD display unit (not shown), etc. At this time, the human presses the top of the optical probe circuit 20B with the fingertip 9. In addition, in step S16, it is determined that a pulse wave of the person 6 to be measured is not detected any more, and thus, without using the pressure actuator 36, a message instructing a human such as a person to be measured to lessen and reduce the stress applied with the fingertip 9 is displayed on the LCD display unit (not shown), etc. At this time, the human lessens the pressure applied with the fingertip 9. As mentioned above, the fingertip 9 of a human such as the person 6 to be measured can be used in place of the pressure actuator 36.

By using the optical probe circuit 20A or 20B of FIG. 9A or 9B and the blood pressure value calibration process of FIG. 19 or of the modified embodiment thereof which are described above, the vessel pulse wave measurement system can perform calibration to convert a blood pressure value voltage of a vessel pulse wave signal to a blood pressure value, by extremely simpler calibration and with higher accuracy than that of the prior art.

Figure 20:
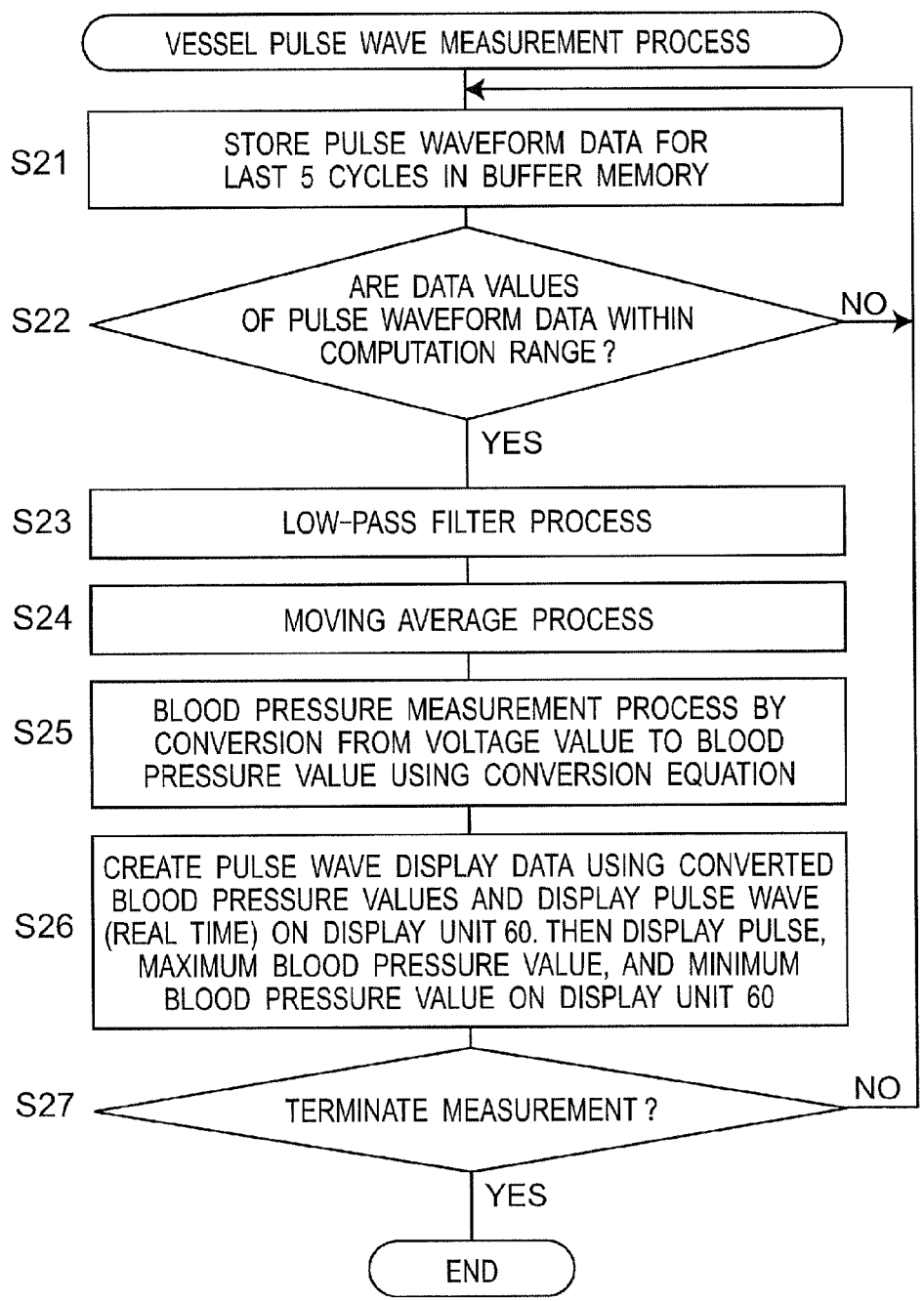
FIG. 20 is a flowchart showing a vessel pulse wave measurement process, which is performed by a vessel pulse wave measurement processing module 51 of the apparatus controller 50 of FIG. 1.

FIG. 20 is a flowchart showing a vessel pulse wave measurement process, which is performed by the vessel pulse wave measurement processing module 51 of the apparatus controller 50 of FIG. 1.

Referring to FIG. 20, in step S21, pulse waveform data (which refers to voltage value data from the A/D converter 31) for the last 5 cycles, for example, is stored in a buffer memory. In step S22, it is determined whether the data values of the pulse waveform data are within a computation range. If YES, then the control flow proceeds to step S23. On the other hand, if NO, then the control flow returns to step S21. In step S23, a low-pass filter process for removing high-frequency noise is performed on the pulse waveform data for 5 cycles. In step S24, a moving average process using a moving average method described with reference to FIGS. 15A and 15B is performed on the pulsation waveform data obtained after the low-pass filter process. Further, in step S25, a blood pressure measurement process by conversion from a voltage value to a blood pressure value using a conversion equation is performed. Further, in step S26, pulse wave display data is created using the converted blood pressure values and a pulse wave (real time) is displayed on the display unit 60 and then a pulse, a maximum blood pressure value, and a minimum blood pressure value are computed and displayed on the display unit 60. In step S27, it is determined whether the measurement is terminated. If YES, then the process ends. On the other hand, if NO, then the control flow returns to step S21.

FIG. 21 is a flowchart showing a sleep state determination process, which is performed by the sleep state determination processing module 53 of the apparatus controller 50 of FIG. 1.

Referring to FIG. 21, in step S31, pulse waveform data for the last 21 cycles, for example, is stored in a buffer memory. In step S32, maximum blood pressure values for 21 cycles Pmax(1) to Pmax(21) and minimum blood pressure values for 21 cycles Pmin(1) to Pmin(21) are computed using the above-described converted maximum blood pressure value and minimum blood pressure value, based on the stored pulse waveform data for 21 cycles, and time t(1) to t(21) are stored in the buffer memory. Then, in step S33, for the 21 cycles (n=1, 2, ..., 21), the following parameters are computed.

The gradient of the maximum blood pressure value Pmax with respect to time (a period of 20 cycles):

P'=(Pmax(21)−Pmax(1))/(t(21)−t(1)),
Pmaxave=average value (Pmax(1) to Pmax(20)), and
Pulse pressure Pp=Pmax(20)−Pmin(20).

Then, in step S34, it is determined whether Pmax(21) decreases by 20% or more with respect to Pmaxave (hereinafter, referred to as a condition 1). If YES, then the control flow proceeds to step S35. On the other hand, if NO, then the control flow returns to step S31. Then, in step S35, it is determined whether the pulse pressure Pp decreases by 20% or more with respect to the average value Pmaxave (hereinafter, referred to as a condition 2). If YES, then the control flow proceeds to step S36. On the other hand, if NO, then the control flow returns to step S31. Then, in step S36, steps S21 to S25 are performed for 3 cycles so as to be shifted every cycle, and a determination about conditions 1 and 2 is made to determine whether conditions 1 and 2 are satisfied over 3 consecutive cycles. If YES, then the control flow proceeds to step S37. On the other hand, if NO, then the control flow returns to step S31. In step S37, it is determined whether the gradient P'>P'th (which is a predetermined threshold value for identifying a gradient angle car and a gradient angle αsa of FIGS. 17A and 17B). If YES, then the control flow proceeds to step S38. On the other hand, if NO, then the control flow proceeds to step S39. In step S38, it is determined that the person 6 to be measured is in an "apnea state" and thus such a fact is displayed on the display unit 60, and the control flow proceeds to step S40. On the other hand, in step S39, it is determined that the person 6 to be measured is in an "awake state" and thus such a fact is displayed on the display unit 60, and the control flow proceeds to step S40. In step S40, it is determined whether the measurement is terminated. If YES, then the process ends. On the other hand, if NO, then the control flow returns to step S31.

In the process of FIG. 21, the number of pieces of data to be processed, a determination branch, etc., such as "20 cycles", "21 cycles", "20%", and "for three cycles" are merely examples and the present invention is not limited thereto. For example, "20%" is a predetermined threshold proportion for determination.

In the above-described embodiment, the above-described processes may be implemented by software or some of the processes may be implemented by a hardware circuit.

Although, in the above-described embodiment, calibration of a maximum blood pressure value and a minimum blood pressure value is performed by a cuff pressure method, the present invention is not limited thereto and other calibration methods may be used.

Differences between the prior art and the present invention will be described below.

The vessel pulse wave measurement method according to the present invention is a measurement method based on a completely different principle than a volume oscillometric method (See, for example, Patent Document 5) and methods using ultrasound (See, for example, Patent Document 6 and Non-Patent Document 1) according to the prior art, etc., and is a non-invasive measurement method, so to speak, a "direct feedback maximization method". The inventors have a specific function and effect that electric characteristics of output voltage with respect to propagation distance shown in, for example, FIGS. 10 to 13 are uniquely measured, and by using the electric characteristics, as shown in FIGS. 16A and 16B, not only the oscillation of a vessel pulse wave but also changes in the base line of a blood pressure value (the DC level of a voltage signal) such as an increase in sympathetic activity and a temporary increase in peripheral vascular resistance due to an awake reaction and a subsequent drop in pulse pressure due to reflex vasodilatation and an excessive increase in sympathetic activity due to apnea, which are unable to be obtained by the non-invasive measurement methods according to the prior art can be measured.

Non-Patent Document 1 describes ultrasonic measurement of the wave intensity of a vessel pulse wave in an arterial system and FIG. 2.44 of Non-Patent Document 1 shows a blood vessel diameter change waveform measured in a human common carotid artery by an ultrasound echo-tracking method and a blood vessel waveform measured in the human common carotid artery by a catheter tip manometer. Though the relation between the blood vessel diameter change waveform and the blood vessel waveform cannot be said to be a complete similarity relation during the entire cardiac cycle, the relation can be considered to be a similarity relation with practically sufficient accuracy. In particular, during an ejection period where the wave intensity of the vessel pulse wave is defined, the relation is a substantially complete similarity relation. By the vessel pulse wave measurement method according to the present invention, a blood vessel diameter change waveform (vessel pulse wave) can be also obtained using an optical oscillation signal.

INDUSTRIAL APPLICABILITY

As described in detail above, a vessel pulse wave measurement system according to the present invention can be used to measure, using a blood vessel pulsation waveform, the state of blood flowing through a blood vessel, such as measurement of blood pressure, specifically as follows.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A vessel pulse wave measurement system that performs vessel pulse wave measurement using an optical probe circuit including (i) a light emitting element that radiates light to a blood vessel through a skin, (ii) a light receiving element that receives, through the skin, reflected light from the blood vessel or transmitted light through the blood vessel, (iii) a drive circuit that drives the light emitting element based on an inputted drive signal, and (iv) a detection circuit that converts the light received by the light receiving element into an electrical signal and outputs the electrical signal, the vessel pulse wave measurement system comprising:

a measurement device configured to directly and synchronously feedback the electrical signal to the drive circuit as the drive signal, generate a self-oscillation signal from the detection circuit, and measure the self-oscillation signal as a vessel pulse wave signal; and a controller configured to control an operating point of at least one of the detection circuit and the drive circuit such that the self-oscillation signal substantially reaches a maximum level thereof, wherein the drive circuit in the optical probe circuit includes first elements having first element values, respectively, and has a first operating point determined by the first element values, wherein the detection circuit in the optical probe circuit includes second elements having second element values, respectively, and has a second operating point determined by the second element values, wherein the optical probe circuit has a third operating point in an electric characteristic representing a level of the electrical signal with respect to a propagation distance of light indicating a distance of light radiated from the light emitting element to reach the light receiving element, the third operating point in the electric characteristic being determined by the first and second operating points, wherein the controller is configured to control the third operating point in the electric characteristic by setting predetermined operating point initial values for the respective first and second operating points, and then control at least one of the first and second operating points such that the self-oscillation signal substantially reaches a maximum level thereof, wherein the electric characteristic has a predetermined extreme value for the level of the electrical signal at a predetermined boundary propagation distance, wherein the controller is configured to control the detection circuit and the drive circuit to operate in at least one range of a first propagation distance range and a second propagation distance range, the first propagation distance range being shorter than the predetermined boundary propagation distance, and the second propagation distance range being longer than the predetermined boundary propagation distance, wherein the controller includes:

a storage device configured to store operating point initial values for first and second operating points corresponding to predetermined operating point initial values in the first propagation distance range, and store operating point initial values for the first and second operating points corresponding to predetermined operating point initial values in the second propagation distance range; and a first switch configured to select one of the operating point initial values in the first propagation distance range and the operating point initial values in the second propagation distance range, and wherein the controller is configured to set the first and second operating points, using the operating point initial values for the first and second operating points corresponding to the operating point initial values selected by the first switch.

2. The vessel pulse wave measurement system as claimed in claim 1, wherein the optical probe circuit includes a plurality of pairs of the light emitting element and the light receiving element, the pairs having different boundary propagation distances, wherein the storage device stores, for each of the pairs, operating point initial values for the first and second operating points corresponding to predetermined operating point initial values in the electric characteristic, wherein the controller includes a second switch configured to select one of the plurality of pairs, and wherein the controller is configured to set the first and second operating points, using the operating point initial values for the first and second operating points of the pair selected by the second switch.

3. A vessel pulse wave measurement system that performs vessel pulse wave measurement using an optical probe circuit including (i) a light emitting element that radiates light to a blood vessel through a skin, (ii) a light receiving element that receives, through the skin, reflected light from the blood vessel or transmitted light through the blood vessel, (iii) a drive circuit that drives the light emitting element based on an inputted drive signal, and (iv) a detection circuit that converts the light received by the light receiving element into an electrical signal and outputs the electrical signal, the vessel pulse wave measurement system comprising:

a measurement device configured to directly and synchronously feedback the electrical signal to the drive circuit as the drive signal, generate a self-oscillation signal from the detection circuit, and measure the self-oscillation signal as a vessel pulse wave signal; and a controller configured to control an operating point of at least one of the detection circuit and the drive circuit such that the self-oscillation signal substantially reaches a maximum level thereof, wherein the drive circuit in the optical probe circuit includes first elements having first element values, respectively, and has a first operating point determined by the first element values, wherein the detection circuit in the optical probe circuit includes second elements having second element values, respectively, and has a second operating point determined by the second element values, wherein the optical probe circuit has a third operating point in an electric characteristic representing a level of the electrical signal with respect to a propagation distance of light indicating a distance of light radiated from the light emitting element to reach the light receiving element, the third operating point in the electric characteristic being determined by the first and second operating points, wherein the controller is configured to control the third operating point in the electric characteristic by setting predetermined operating point initial values for the respective first and second operating points, and then control at least one of the first and second operating points such that the self-oscillation signal substantially reaches a maximum level thereof, wherein the measurement device is configured to compute a plurality of determination parameters based on the measured vessel pulse wave signal for a predetermined number of cycles, and determine whether a person to be measured is in one of an awake state and an apnea state, based on the plurality of determination parameters, the plurality of determination parameters including a gradient of a maximum blood pressure value with respect to time, an average value of the maximum blood pressure values, and a pulse pressure, which is a difference between a maximum blood pressure value and a minimum blood pressure value, wherein the measurement device is configured to determined that the person to be measured is in an awake state, (a) when a maximum blood pressure value at a predetermined time decreases by a predetermined first threshold proportion or more with respect to the average value of the maximum blood pressure value, (b) when the pulse pressure decreases by a predetermined second threshold proportion or more with respect to the average value of the maximum blood pressure value during a predetermined number of consecutive cycles, and (c) when the gradient of the maximum blood pressure value with respect to the time exceeds a predetermined threshold value, and wherein the measurement device is configured to determined that the person to be measured is in an apnea state when the gradient is equal to or smaller than the threshold value.

* * * * *